(12) United States Patent
Eftekhari et al.

(10) Patent No.: US 9,327,053 B2
(45) Date of Patent: May 3, 2016

(54) ARTIFICIAL BONE NANOCOMPOSITE AND METHOD OF MANUFACTURE

(71) Applicant: Samin Eftekhari, Markham, Ontario (CA)

(72) Inventors: Samin Eftekhari, Markham (CA); Habiba Bougherara, Toronto (CA)

(73) Assignee: Samin Eftekhari, Markham, Ontario (CA)

( * ) Notice: Subject to any disclaimer, the term of this patent is extended or adjusted under 35 U.S.C. 154(b) by 0 days.

(21) Appl. No.: 14/684,939

(22) Filed: Apr. 13, 2015

(65) Prior Publication Data

US 2015/0231304 A1 Aug. 20, 2015

Related U.S. Application Data

(63) Continuation of application No. 14/624,613, filed on Feb. 18, 2015, now abandoned.

(60) Provisional application No. 61/941,492, filed on Feb. 19, 2014.

(51) Int. Cl.
| | |
|---|---|
| *A61L 27/46* | (2006.01) |
| *A61L 27/48* | (2006.01) |
| *A61L 27/56* | (2006.01) |
| *D01D 5/00* | (2006.01) |
| *A61L 31/12* | (2006.01) |
| *A61L 31/14* | (2006.01) |

(52) U.S. Cl.
CPC .................. *A61L 27/48* (2013.01); *A61L 27/46* (2013.01); *A61L 27/56* (2013.01); *A61L 31/127* (2013.01); *A61L 31/129* (2013.01); *A61L 31/146* (2013.01); *D01D 5/00* (2013.01); *A61L 2400/12* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,969,913 A | 11/1990 | Ojima | |
| 5,082,808 A | 1/1992 | Nonami et al. | |
| 5,141,510 A | 8/1992 | Takagi et al. | |
| 5,152,791 A | 10/1992 | Hakamatsuka et al. | |
| 5,425,769 A | 6/1995 | Snyders, Jr. | |
| 5,487,933 A | 1/1996 | White | |
| 5,634,956 A | 6/1997 | Suh et al. | |
| 5,683,462 A | 11/1997 | Schmidt | |
| 5,769,897 A | 6/1998 | Harle | |
| 5,814,681 A | 9/1998 | Hino et al. | |
| 6,149,688 A | 11/2000 | Brosnahan et al. | |
| 6,206,924 B1 | 3/2001 | Timm | |
| 6,395,036 B1 | 5/2002 | Czernuszka et al. | |
| 6,537,589 B1 | 3/2003 | Chae et al. | |
| 6,589,590 B2 | 7/2003 | Czernuszka et al. | |
| 6,692,448 B2 | 2/2004 | Tanaka et al. | |
| 6,932,610 B2 | 8/2005 | Ono et al. | |
| 7,018,212 B2 | 3/2006 | Zeeff | |
| 7,039,225 B2 | 5/2006 | Tanaka et al. | |
| 7,052,518 B2 | 5/2006 | Irie et al. | |
| 7,662,864 B2 * | 2/2010 | Kanamathareddy . | A61K 9/0024 514/197 |
| 7,871,561 B2 | 1/2011 | Kokubo et al. | |
| 7,879,093 B2 | 2/2011 | Wei et al. | |
| 8,003,611 B2 | 8/2011 | Kamitakahara et al. | |
| 8,210,852 B2 | 7/2012 | Miller et al. | |
| 8,366,786 B2 | 2/2013 | Shoji | |
| 8,455,038 B2 | 6/2013 | Amaya et al. | |
| 8,586,101 B2 | 11/2013 | Lidgren | |
| 8,663,326 B2 | 3/2014 | Osman | |
| 8,709,452 B2 | 4/2014 | Varghese et al. | |
| 2007/0207186 A1* | 9/2007 | Scanlon .................... | A61F 2/07 424/424 |
| 2008/0195198 A1 | 8/2008 | Asgari | |
| 2009/0270527 A1* | 10/2009 | Lin .......................... | A61K 6/08 523/116 |
| 2013/0017232 A1 | 1/2013 | Varghese et al. | |

OTHER PUBLICATIONS

Armentano, I. et al., "Multifunctional nanostructured PLA materials for packaging and tissue engineering," ScienceDirect: Progress in Polymer Science, 2013, pp. 1720-1747, vol. No. 38, Elsevier Ltd.

Ma, Peter X. et al., "Engineering new bone tissue invitro on highly porous poly(hydroxyl acids)/hydroxyapatite composite scaffolds," Journal of Biomedical Materials research, 2001, pp. 284-293, vol. No. 54, John Wiley & Sons, Inc.

Majdzadeh-Ardakani, Kazem et al., "Optimization of mechanical properties of thermoplastic starch/clay nanocomposites," ScienceDirect: Carbohydrate Polymers, 2010, pp. 547-554, vol. No. 79, Elsevier Ltd.

Nieddu, Erika et al., "Preparation and biodegradation of clay composites of PLA," ScienceDirect: Reactive & Functional Polymers, 2009, pp. 371-379, vol. No. 69, Elsevier Ltd.

Pei, Aihua et al., "Functionalized cellulose nanocrystals as biobased nucleation agents in poly(L-lactide) (PLLA)-Crystallization and mechanical property effects," ScienceDirect: Composites Science and Technology, 2010, pp. 815-821, vol. No. 70, Elsevier Ltd.

Perez, Roman A. et al, "Naturally and synthetic smart composite biomaterials for tissue regeneration," ScienceDirect: Advanced Drug Delivery Reviews, 2013, pp. 471-496, vol. No. 65, Elsevier B.V.

(Continued)

*Primary Examiner* — Peter A Salamon
(74) *Attorney, Agent, or Firm* — Renner, Otto, Boisselle & Sklar, LLP

(57) ABSTRACT

A composition suitable for bone replacement is provided. The composition is a nanocomposite matrix, resembling both the structure and the properties of natural bone, including morphology, composition and mechanical characteristics. The nanocomposite is preferably porous and comprises: (1) micro or nano scale cellulose crystals or fibers; (2) hydroxyapatite nanoparticles; (3) Poly L-Lactide Acid or poly glycolic acid; and (4) a coupling agent, for example a surfactant, preferably an anionic surfactant such as sodium dodecyl sulfate. The composition is useful as an artificial bone replacement or bone graft, is preferably biomimetic, and can be suitable for use, for example, in trabecular bone substitution and osteoanagenesis applications. A method of fabrication of the nanocomposite is also provided.

17 Claims, 13 Drawing Sheets

(56) References Cited

OTHER PUBLICATIONS

Rhim, Jong-Whan et al., "Tensile, water vapor barrier and antimicrobial properties of PLA/nanoclay composite films," ScienceDirect: LWT—Food Science and Technology, 2009, pp. 612-617, vol. No. 42, Elsevier Ltd.

Roether, J.A. et al., "Developement and invitro characterization of novel bioresorbable and bioactive composite materials based on polylactide foams and bioglass for tissue engineering applications," Biomaterials, 2002, pp. 3871-3878, vol. No. 23, Elsevier Science Ltd.

Schrauwen, Bernard A. G. et al., "Intrinsic deformation of semicrystalline polymers," Macromolecules, 2004, pp. 6069-6078, vol. No. 37, American Chemical Society.

Sturcova, Adriana et al.,"Elastic modulus and stress-transfer properties of tunicate cellulose whiskers," Biomacromolecules, 2005, pp. 1055-1061, vol. No. 6, American Chemical Society.

Zhang, Ruiyun et al., "Poly(alpha-hydroxyl acids)/hydroxyapatite porous composites for bone-tissue engineering. I. Preparation and morphology," Journal of Biomedical Material Research, 1999, pp. 446-455, vol. No. 44, John Wiley & Sons, Inc.

Li, Bo et al., "Organically modified rectorite toughened poly(lactic acid): Nanostructures, crystallization and mechanical properties," ScienceDirect: European Polymer Journal, 2009, pp. 2996-3003, vol. No. 45, Elsevier Ltd.

Lewitus, D. et al., "The Effect of Nanoclays on the Properties of PLLA-modified Polymers Part 1: Mechanical and Thermal Properties," Journal of Polymers and the Environment, 2006, pp. 171-177, vol. No. 14, Springer Science +Business Media, Inc.

Kim, Hae-Won et al., "Bioactivity and osteoblast responses of novel biomedical nanocomposites of bioactive glass nanofiber filled poly(lactic acid)," Wiley InterScience, 2007, pp. 651-663, Wiley Periodicals, Inc.

Gay, Sandrine et al., "Preparation and characterization of dense nanohydroxyapatite/PLLA composites," ScienceDirect: Materials Science and Engineering C, 2009, pp. 172-177, vol. No. 29, Elsevier B.V.

Aydin, Erkin et al., "Hydroxyapatite nanorod-reinforced biodegradable poly (L-lactic acid) composites for bone plate applications," Journal of Materials Science: Materials in Medicine, 2011, pp. 2413-2427, vol. No. 22, Springer Scuebce+Business Media, LLC.

Xiao, Yumei et al., "Preparation of nano-HA/PLA composite by modified-PLA for controlling the growth of HA crystals," ScienceDirect: Materials Letters, 2007, pp. 59-62, vol. No. 61, Elsevier B.V.

Gupta, A.P. et al., "New emerging trends in synthetic biodegradable polymers—Polylactide: a critique," ScienceDirect: European Polymer Journal, 2007, pp. 4053-4074, vol. No. 43, Elsevier Ltd.

Agrawal, C. Mauli et al., "Biodegradable polymeric scaffolds for musculoskeletal tissue engineering," Journal of Biomedical Materials Research, 2001, pp. 141-150, vol. No. 55, John Wiley & Sons, Inc.

Grizzi, I. et al., "Hydrolytic degradation of devices based on poly(DL-lactic acid) size-dependence," Biomaterials, 1995, pp. 305-311, vol. No. 16, Elsevier Science Limited.

Lasprilla, Astrid J.R. et al., "Poly-lactic acid synthesis for application in biomedical devices—a review," ScienceDirect: Biotechnology Advances, 2012, pp. 321-328, vol. No. 30, Elsevier Inc.

Ciobanu, G. et al., "Polyurethane-Hydroxyapatite Bionanocomposites: Development and Characterization," Chemical Bulletin of Politehnica, University of Timisoara Romania, 2009, pp. 57-60, vol. No. 54.

Schiller, Carsten et al, "Geometrically structured implants for cranial reconstruction made of biodegradable polyesters and calcium phosphate/calcium carbonate," ScienceDirect: Biomaterials, 2004, pp. 1239-1247, vol. No. 25, Elsevier Ltd.

Woo, Kyung Mi et al., "Supression of apoptosis by enhanced protein adsorption on polymer/hydroxypatite composite scaffolds," ScienceDirect: Biomaterials, 2007, pp. 2622-2630, vol. No. 28, Elsevier Ltd.

Wan, Y.Z et al., "Biomimetic synthesis of hydroxyapatite/bacterial cellulose nanocomposites for biomedical applications," ScienceDirect: Materials Science and Engineering C, 2007, pp. 855-864. vol. No. 27, Elsevier B.V.

Chen, Guoping et al., "Development of biodegradable porous scaffolds for tissue engineering," Materials Science and Engineering C, 2001, pp. 63-69, vol. No. 17, Elsevier Science B.V.

Guan, Limin et al., "Preparation and characterization of a highly macroporous biodegradable composite tissue engineering scaffold," Wiley InterScience, 2004, pp. 480-487, Wiley Periodicals, Inc.

Teixeria, S. et al., "Physical characterization of hydroxypatite porous scaffolds for tissue engineering," ScienceDirect: Materials Science and Engineering C, 2009, pp. 1510-1514, vol. No. 29, Elsevier B.V.

Russias, J. et al., "Fabrication and mechanical properties of PLA/HA composites: a study of in vitro degregation," ScienceDirect: Materials Science and Engineering C, 2006, pp. 1289-1295, vol. No. 26, Elsevier B.V.

Gouma, P. et al., "Nano-hydroxypatite-Cellulose acetate composites for growing of bone cells," ScienceDirect: Materials Science and Engineering C, 2012, pp. 607-612, vol. No. 32, Elsevier B.V.

Zimmermann, Kristen A. et al., "Biomimetic design of a bacterial cellulose/hydroxypatite nanocomposite for bone healing application," ScienceDirect: Materials Science and Engineering C, 2011, pp. 43-49, vol. No. 31, Elsevier B.V.

Zadegan, S. et al., "Synthesis and biocompatibility evaluation of cellulose/hydroxyapatite nanocomposite scaffold in 1-n-allyl-3-methylimidazolium chloride," ScienceDirect: Materials Science and Engineering C, 2011, pp. 954-961, vol. No. 31, Elsevier B.V.

Nejati, E. et al., "Needle-like nano hydroxyapatite/poly(L-lactide acid) composite scaffold for bone tissue engineering application," ScienceDirect: Materials Science and Engineering C, 2009, pp. 942-949, vol. No. 29, Elsevier B.V.

El-Kady, Abeer M. et al., "Development, characterization, and in vitro bioactivity studies of sol-gel bioactive glass/poly(L-lactide) nanocomposite scaffolds," ScienceDirect: Materials Science and Engineering C, 2010, vol. No. 30, Elsevier B.V.

Tian, Ting et al., "Fabrication of bioactive composite by developing PLLA onto the framework of sintered HA scaffold," ScienceDirect: Materials Science and Engineering C, 2008, pp. 51-56, vol. No. 28, Elsevier B.V.

Wei, Guobao et al., "Structure and properties of nano-hydroxyapatite/polymer composite scaffolds for bone tissue engineering," ScienceDirect: Biomaterials, 2004, pp. 4749-4757, vol. No. 25, Elsevier Ltd.

Xu, Tao et al., "Modification of nanostructured materials for biomedical applications," ScienceDirect: Materials Science and Engineering C, 2007, pp. 579-594, vol. No. 27, Elsevier B.V.

Liu, D.Y. et al., "Characterisation of solution cast cellulose nanofibre-reinforced poly(lactic acid)," eXPRESS Polymer Letters, 2010, pp. 26-31, vol. No. 4, Issue No. 1, BME-PT.

Bondeson, Daniel et al., "Optimization of the isolation of nanocrystals from microcrystalline cellulose by acid hydrolysis," Cellulose, 2006, pp. 171-180, vol. No. 13, Springer.

Eichhorn, S.J. et al., "Review: current international research into cellulose nanofibres and nanocomposites," Journal of Materials Science, 2010, pp. 1-33, vol. No. 45, Issue No. 1, Springer Science+Business Media, LLC.

Frone, A.N. et al., "Cellulose Fiber-Reinforced Polylactic Acid," Polymer Composites, 2011, pp. 976-985, Society of Plastics Engineers.

Gomes, M.E. et al., "Alternative tissue engineering scaffolds based on starch: processing methodologies, morphology, degradation and mechanical properties," Materials Science and Engineering C, 2002, pp. 19-26, vol. No. 20, Elsevier Science B.V.

Luong, Nguyen Dang et al., "Surface modification of poly(L-lactide) electrospun fibers with nanocrystal hydroxyapatite for engineered scaffold applications," ScienceDirect: Materials Science and Engineering C, 2008, pp. 1242-1249, vol. No. 28, Elsevier B.V.

Pilia, Marcello et al., "Development of Composite Scaffolds for Load-Bearing Segmental Bone Defects," BioMed Research International, 2013, pp. 1-15, vol. No. 2013, Hindawi Publishing Corporation.

(56) References Cited

OTHER PUBLICATIONS

Noh, Kyung-Tae et al., "Composite nanofiber of bioactive glass nanofiller incorporated poly(lactic acid) for bone regeneration," ScienceDirect: Materials Letters, 2010, pp. 802-805, vol. No. 64, Elsevier B.V.

Hayati, Amir Nemati et al., "Characterization of poly(3-hydroxybutyrate)/nano-hydrozyapatite composite scaffolds fabricated without the use of organic solvents for bone tissue engineering applications," SciVerse ScienceDirect: Materials Science and Engineering C, 2012, pp. 416-422, vol. No. 32, Elsevier B.V.

Kellomaki, Minna et al., "Bioabsorbable scaffolds for guided bone regeneration and generation," Biomaterials, 2000, pp. 2495-2505, vol. No. 21, Elsevier Science Ltd.

Joulazadeh, Mehmaz et al., "Effect of process variables on mechanical properties if polyurethane/clay nanocomposites," Polymer Advanced Technologies, 2010, pp. 263-271, vol. No. 21, John Wiley & Sons, Ltd.

Nejati, E. et al., "Synthesis and characterization of nano-hydroxyaptite rods/poly(L-lactide acid) composite scaffolds for bone tissue engineering," ScienceDirect: Composites: Part A, 2008, pp. 1589-1596, vol. No. 39, Elsevier Ltd.

Mathew, Aji P. et al., "The Effect of Morphology and Chemical Characteristics of Cellulose Reinforcements on the Crystallinity of Polylactic Acid," Journal of Applied Polymer Science, 2006, pp. 300-310, vol. No. 101, Wiley Periodicals, Inc.

Hsu, Yung-Yueh et al., "Effect of polymer foam morphology and density on kinetics of in vitro controlled release of isoniazid from compressed foam matrices," Journal of Biomedical Materials Research, 1997, pp. 107-116, vol. No. 35, John Wiley & Sons, Inc.

Ma, Zuwei et al., "Biodegradable Polyurethane Ureas with Variable Polyester or Polycarbonate Soft Segments: Effects of Crystallinity, Molecular Weight, and Composition on Mechanical Properties," BioMacromolecules, 2011, pp. 3265-3274, vol. No. 12, American Chemical Society.

Amini, Ami R. et al., "Bone Tissue Engineering: Recent Advances and Challenges," Crital Reviews in Biomedical Engineering, 2012, pp. 363-408, vol. No. 40, Issue No. 5, National Institutes of Health.

Eftekhari, Samin et al., "Fabrication and characterization of novel biomimetic PLLA/cellulose/hydroxyapatite nanocomposite for bone repair applications," ScienceDirect: Materials Science and Engineering C, 2014, pp. 120-125, vol. No. 39, Elsevier B.V.

Gning, P.B. et al., "Influence of process and test parameters on the mechanical properties of flax/epoxy composites using response surface methodology," Journal of Materials Science, 2011, pp. 6801-6811, vol. No. 46, Springer Science+Business Media, LLC.

Graupner, Nina et al., "Natural and man-made cellulose fibre-reinforced poly(lactic acid) (PLA) composites: An overview about mechanical characteristics and application areas," ScienceDirect: Composites: Part A, 2009, pp. 810-821, vol. No. 40, Elsevier Ltd.

Zerda, Adam S. et al., "Intercalated Clay Nanocomposites: Morphology, Mechanics, and Fracture Behavior," Journal of Polymer Science: Part B: Polymer Physics, 2001, pp. 1137-1146, vol. No. 39, John Wiley & Sons, Inc.

Goetz, Lee et al., "A novel nanocomposite film prepared from crosslinked cellulosic whiskers," ScienceDirect: Carbohydrated Polymers, 2009, pp. 85-89, vol. No. 75, Elsevier Ltd.

Martins, Ana M. et al., "Responsive and in situ-forming chitosan scaffolds for bone tissue engineering applications: an overview of the last decade," Journal of Materials Chemistry, 2010, pp. 1638-1645, vol. No. 20, The Royal Society of Chemistry.

Espert, Ana et al., "Comparison of water absorption in natural cellulosic fibers from wood and one-year crop in polypropylene composites and its influence on their mechanical properties," ScienceDirect: Composites: Part A, 2004, pp. 1267-1276, vol. No. 35, Elsevier Ltd.

Okomoto, Masami et al., "Synthetic biopolymer nanocomposites for tissue engineering," ScienceDirect: Progress in Polymer Science, 2013, pp. 1487-1503, vol. No. 38, Elsevier Ltd.

\* cited by examiner

ARTIFICIAL BONE NANOCOMPOSITE AND METHOD OF MANUFACTURE

This patent application is a continuation of non-provisional patent application Ser. No. 14/624,613, filed Feb. 18, 2015, which claims priority to U.S. provisional patent application 61/941,492, filed Feb. 19, 2014, each of which is incorporated herein by reference in its entirety.

FIELD OF THE INVENTION

The present invention relates to artificial bone. More particularly, the present invention relates to a nanocomposite composition, use of the composition for bone repair applications, and a method of preparing the composition.

BACKGROUND OF THE INVENTION

Bone fractures are one of the most common forms of injury. The second most common transplantable tissue after blood is bone. Each year, approximately 170,000 bone fractures in the United States fail to heal. In order to encourage the bone healing process, bone grafts are often needed. These grafts are external bone tissue taken from the patient or from an external source. Bone taken from the patient can cause problems in the donor site, and bone taken from other sources has a considerable chance of being rejected by the patient's body. Accordingly, there is a need for biocompatible artificial bone substitutes.

The mechanical properties of human bone vary tremendously according to the location and function in the body. The mechanical properties and biodegradation rate of any artificial bone should be tailored to match the properties of the surrounding bone at the damaged site.

Natural bone is a complex nanocomposite matrix comprising collagen fibers and calcium phosphate minerals. Artificial nanocomposites mimicking certain properties of bone have been shown with limited success. A plurality of complex variables has made production of artificial bone a significant challenge.

Poly L-Lactic Acid (PLLA) is a biocompatible and biodegradable polymer that has been used widely for biomedical applications. However, PLLA based composites have had some drawbacks, including low mechanical properties and acidic degradation by-products.

Hydroxyapatite (HA) has many similarities with the calcium phosphates of natural bone, and has been used with limited but promising effect in biomimetic applications.

Although natural ceramic/polymer nanocomposites with certain, limited, functionality have been suggested, many crucial challenges remain to be overcome. One of the ongoing challenges is increasing the mechanical strength without sacrificing the elongation at break (toughness) of composites made up of PLLA and HA. Prior art PLLA/HA composites crack under stress due to the brittle nature of HA and their load-bearing property is less than desirable.

One prior art approach is utilizing biopolymer nanofibres or microcrystals as a reinforcing agent. The incorporation of more flexible reinforcing agents such as cellulose fibers or crystals has been suggested to reduce the composite brittleness. Moreover, the cellulose, such as cotton sourced cellulose microcrystals or any plant-sourced cellulose nanofibres, appears to simulate the collagen fibrils existing in natural bone. However, use of such materials has had significant challenges, related to their hydrophilic nature. Specifically, such materials have low compatibility with polymeric matrices having a hydrophobic nature. This causes poor mechanical and water absorption properties, and difficulty in utilizing them to make a suitable artificial bone.

The main challenge in fabrication of the PLLA/HA/cellulose nanocomposites or previously developed PLLA and HA by other scientists is weak interfacial bonding that appears to inversely affect the reinforcing efficiency of the HA particles. Use of the two together has been taught against—non-polar polymers including PLLA have almost no affinity to the polar reinforcing agents such as HA or cellulose. This is generally because cellulose and HA have a hydrophilic nature, whereas PLLA has hydrophobic characteristics, resulting in significant challenges when interfacial bonding. Moreover, the strong affinity of cellulose crystals to each other encourages their aggregation and sedimentation, which is undesirable when using them in a composite. Another challenge is the undesirable high water absorption properties of natural fibers such as cellulose fibers, resulting in sooner than expected biodegradation, an undesired size change of the implant, and unmet mechanical strength in vivo.

An artificial bone-like composite is desirable, for use in grafting, implants, or other bone replacement or healing therapies.

BRIEF SUMMARY OF THE INVENTION

According to the present invention, there is provided two series of nanocomposite composition designed to mimic certain types of natural human bone. The nanocomposite composition comprises: Poly L-Lactic Acid (PLLA) or poly glycolic acid (PLGA); reinforced with microcrystalline or nanocrystalline cellulose fibres or crystals, preferably cotton sourced microcrystalline cellulose or any plant-sourced cellulose nanofibres; hydroxyapatite (HA) nanoparticles; and a coupling agent, for example a surfactant, preferably an anionic surfactant such as Sodium Dodecyl Sulphate (SDS).

The composition materials, weight fractions and ratio of the constituents disclosed herein are able to, depending upon the application desired and materials chosen, provide specific handling characteristics during processing and fabrication and final properties prior to transplantation or grafting.

Since the composition of the nanocomposite materials affects the resulting mechanical behaviour, it is an object of the present invention to provide mechanical and water absorption properties suitable for use in bone repair applications.

Another object of the invention is to overcome the challenges of dispersing hydrophilic cellulose and hydroxyapatite nanoparticles in a hydrophobic PLLA or PLGA solution by utilizing a coupling agent, such as SDS, and a unique fabrication method.

It is another object of the invention to provide nanocomposites with desired chemical, thermal and mechanical properties by selecting specific weight ratio ranges for the reinforcing agents.

A further object of the invention is to provide a nanocomposite having the desired mechanical and water absorption properties as well as a desired porous structure, through the use of a porogen such as a salt (preferably a chloride salt) or a sugar, in the fabrication process.

Yet a further object of the invention is a composition comprising: (a) Poly L-Lactide acid (PLLA), or poly glycolic acid (PLGA); (b) micro or nano scale cellulose crystals or fibers; (c) hydroxyapatite (HA) nanoparticles, and (d) a coupling agent, wherein the composition is in the form of a porous nanocomposite matrix.

In certain embodiments, the micro or nano scale cellulose crystals or fibers in the composition are a cotton sourced microcrystalline cellulose (MCC). In certain embodiments, the coupling agent in the composition is an anionic surfactant, for example, sodium dodecyl sulphate (SDS).

In certain embodiments, the weight fraction of PLLA in the composition is 40 to 57 $W_t$ %. In certain embodiments, the summation of the weight fraction of MCC+HA in the composition is 28 to 40 $W_t$ %. In certain embodiments, the weight fraction of SDS in the composition is 14 to 20 $W_t$ %. In certain embodiments, the weight ratio of MCC to HA in the composition is 1:1 to 4:1.

In certain embodiments, the micro or nano scale cellulose crystals or fibers in the composition have a mean particle size of less than 20 μm and an aspect ratio of less than 4. In certain embodiments, the HA nanoparticles in the composition have a mean particle size of less than 200 nm and a surface area of about 14 $m^2/g$. In certain embodiments, the PLLA has an average molecular weight of at least about 85000 g/mol, a crystallinity of about 37%, and a glass transition temperature of about 60-65° C.

According to a further embodiment of the invention is provided the use of such a composition as an artificial bone substitute, graft or filling. The use can be to replace, repair or graft a trabecular bone.

According to a further embodiment of the invention, the composition can be used as a 3-D printed patient-tailored bone substitute or a 3-D printed biodegradable biomaterial, or as a fractured bone fixation instrument such as a biodegradable screw.

According to a further embodiment of the invention is provided a method for manufacturing a composition as hereindescribed, comprising (a) pretreating the cellulose crystals or fibers and the HA nanoparticles to promote disaggregation; and (b) dispersing the cellulose crystals or fibers and the HA nanoparticles in a matrix of the PLLA or PLGA in a generally homogeneous manner.

According to certain embodiments, the pretreating comprises ultrasonication and incorporation of the coupling agent.

According to a further embodiment of the invention is provided a method for manufacturing a composition as herein described, comprising: dissolution of the PLLA or PLGA in an organic solvent to form a dissolved PLLA or PLGA; drying the HA nanoparticles to remove water, then transferring the HA nanoparticles to a solvent to form a dispersion of HA nanoparticles in said solvent; ultrasonicating the cellulose crystals or fibers in solvent to form a ultrasonicated cellulose dispersion in said solvent; combining the dispersion of HA nanoparticles and the ultrasonicated cellulose dispersion and adding the coupling agent to form a combined dispersion; combining the dissolved PLLA or PLGA and the combined dispersion to obtain a generally homogeneous colloidal suspension; optionally adding a porogen; molding and freezing the generally homogeneous colloidal suspension to form a solidified nanocomposite mass; freeze drying the solidified nanocomposite mass to sublimate the solvent under vacuum and form the composition; optionally removing excess coupling agent by floating the resultant composition in water.

According to certain embodiments, the organic solvent and the solvent are both 1,4-dioxane. In certain embodiments, the drying is by a solvent extraction. In certain embodiments, the solvent extraction uses, sequentially, water, acetone, ethanol, and 1,4-dioxane. In certain embodiments, the coupling agent is SDS. In certain embodiments, the porogen is a sodium chloride salt or a sugar.

Other objects of the invention will be more fully set forth in the following description thereof.

BRIEF DESCRIPTION OF THE DRAWINGS

Further understanding of the nature, objects and advantages of the present invention will be readily appreciated by reference to the following detailed description when read in conjunction with the accompanying drawings wherein.

DETAILED DESCRIPTION OF THE INVENTION

Figure 1:
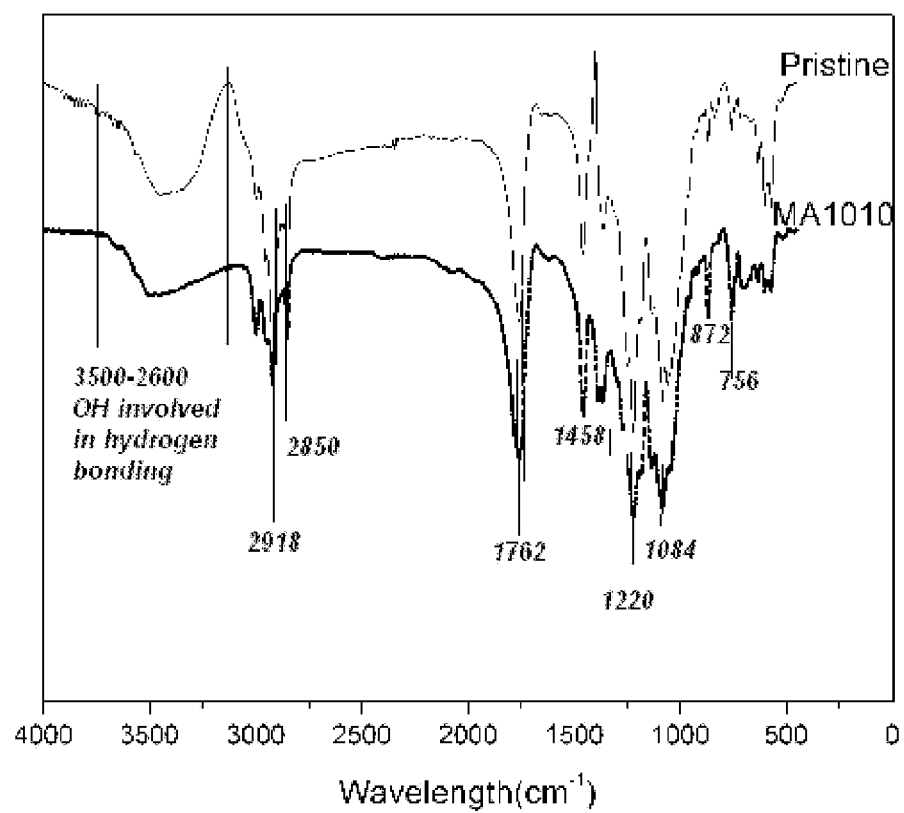
FIG. 1 shows an FTIR graph of certain nanocomposite compositions of the present invention.

The present invention is a novel nanocomposite composition which mimics certain characteristics of bone. In certain embodiments, the nanocomposition can be made to mimic the characteristics of specific types of bone, such as the trabecular bone. The nanocomposite compositions are useful in bone repair applications, such as: osseous repair, bone graft substitutions including 3-D printed patient-tailored bone substitutes, substance delivery carriers, or fractured bone fixation instruments such as biodegradable screws.

The composition is made from: (1) Poly L-Lactide Acid (PLLA) or poly glycolic acid (PLGA), preferably PLLA; (2) micro or nano cellulose crystals or fibres, preferably cotton sourced microcrystalline cellulose (MCC) or any plant-sourced cellulose nanofibres, most preferably MCC; (3) calcium phosphate containing nanoparticles, preferably hydroxyapatite (HA) nanoparticles; and (4) a coupling agent, such as a surfactant, preferably an anionic surfactant, most preferably sodium dodecyl sulphate (SDS).

The composition is a porous nanocomposite matrix, with the PLLA or PLGA providing the backbone. The composition provides excellent bone-like structure, and can be used as a bone graft, an artificial bone substitute, or a filling to replace a lost or eroded portion of bone. The composition is particularly good as a trabecular bone substitute, but artificial bone mimicking the properties of other types of bones are certainly contemplated, and well within the present teachings.

The process for manufacturing the composition is generally as follows. (1) The PLLA or PLGA is dissolved in an organic solvent, such as 1,4 dioxane. (2) Dry HA nanoparticles are also dispersed in a second, compatible solvent. In a preferred embodiment, this second, compatible solvent is the same organic solvent as that used for dissolving the PLLA or PLGA, for example, 1,4 dioxane. It has been found that it is highly preferable that the HA nanoparticles be as dry as possible. Since the HA nanoparticles are generally hydroscopic in nature, it has been found to be highly preferable to actively dry the HA nanoparticles shortly before dispersing in 1,4 dioxane. This drying step can be by any known means, but it has been found that a solvent extraction/centrifugation, utilizing, sequentially, water, acetone, ethanol and 1,4-dioxane, works well. (3) The cellulose is dispersed in a compatible solvent. In a preferred embodiment, this compatible solvent is the same organic solvent as that used for dispersing the HA nanoparticles, for example, 1,4 dioxane. It has been found advantageous to ultrasonicate the cellulose, especially when using MCC, when dispersing the cellulose in solvent. It appears that ultrasonication breaks up the MCC into smaller, possibly nano-sized particles, and aids in obtaining a homogeneous dispersion. The dispersion of MCC into the solvent may be done separately, or in the same solvent and suspension, as the HA nanoparticle suspension described in step (2). However, preferably, the dispersion of MCC in solvent is performed separately, then combined in step (4), below. (4) In methods where the cellulose and HA dispersions are made separately, they are then combined. A coupling agent is added to this combined dispersion. The coupling agent is selected to aid in the coupling of the cellulose and HA, generally hydrophilic, to the generally hydrophobic PLLA/PLGA. The term "coupling agent" means any agent that aids in coupling the generally hydrophilic cellulose and HA to the generally hydrophobic PLLA/PLGA. It has been found that an anionic surfactant is particularly effective as a coupling agent. In a preferred embodiment, SDS can be used as the coupling agent, and provides excellent results. Without being limited to any specific theory, it is believed that they hydrophilic head of the SDS molecule adsorbs on the surface of the cellulose and HA particles, bonding to $Ca^{2+}$ through ionic phosphate and carboxylate groups of the HA and cellulose. (5) The combined dispersion of HA and cellulose, containing coupling agent, is combined with the PLLA/PLGA in solvent from step (1), to form a generally homogeneous colloidal suspension. This colloidal suspension forms the basis for the artificial bone composition. (6) For certain desired porosities for the finished product, it is optimal to add a porogen at this stage. The porogen is incorporated into the colloidal suspension and provides additional porosity to the composition when it is later washed out. Any known porogen can be used; it has been found that sodium salts, such as sodium chloride, and simple sugars, are both excellent porogens, providing excellent porosity in the final product. (7) The generally homogeneous colloidal suspension, optionally containing porogen, can be placed in a mold of the desired shape and size, and frozen to form a solidified nanocomposite mass. The solvent is then removed, for example, through freeze drying to sublimate the solvent under vacuum, forming the composition. It is expected that, alternatively, the generally homogeneous colloidal suspension can also be used as a substrate for 3D printing into a desired shape. Depending on the type of the 3-D printing machine the desirable composition powder can be used as starting material. In such case the powder include the appropriate ratio and weight fraction of constituents (PLLA/MCC/HA/SDS) will be melted and the viscose liquid acts as feeding solution of 3-D printing machine. This permits extremely accurate formation of the desired shape or structure of the composition. In this alternative manufacturing method, it is expected that the solvent would be sublimated in the 3D printing process, though a freeze drying step may also be necessary. (8) The use of porogen in 3-D fabrication method can be eliminated. Optionally, excess coupling agent can also be removed by floating or soaking the composition in an appropriate solvent such as water.

As would be readily appreciated, the relative amounts of each of the components of the composition have a significant impact on the overall qualities of the artificial bone produced, including the rigidity, strength, compression profile, porosity, and the like. Generally, the weight ratios of components utilized to make the composition will remain constant in the final product, with the exception of the coupling agent (excess coupling agent can be removed), and, of course, the porogen which is entirely removed. It has been found that a composition having about 40-57 wt % PLLA, 29-40 wt % cellulose and HA, and 14-20 wt % SDS provides set of nanocomposites with excellent bone-like properties. It has also been found that a weight ratio of cellulose to HA of about 1:1 to about 4:1 is desirable. It has been found that nanocomposite having 57 wt % PLLA, 29 wt % of (cellulose and HA), and 14 wt % of SDS, with ratio of cellulose to HA of about 4 provides excellent results.

It has been found that increasing the HA/cellulose content generally increases the crystallinity of the composition. Increasing the content of the cellulose and HA generally increases the mechanical strength of the composition, and decreases the amount of absorbed water in the composition. Compositions of various component content ratios are possible, each with slightly different, but often useful, bone-like characteristics, as further exemplified below. As can be appreciated, bone is an extremely complex structure, and in certain applications, it may be desirable that a portion of the bone substitute is more flexible or stronger than the rest of the bone. Accordingly, a plurality of different compositions of the present invention, having, for example, different porosities or different HA/cellulose content, can be combined in one mold to provide an artificial bone having different properties at different locations.

As might also be expected, it was found that the size of the components used had an effect on the quality and properties of the composition. It was found that utilizing cellulose crystals having a mean particle size of less than 20 μm and an aspect ratio of less than 4 provided excellent results. HA nanoparticles having a mean particle size of less than 200 nm and a surface area of about 14 $m^2/g$ provided excellent results.

PLLA with an average molecular weight of at least about 85000 g/mol, a crystallinity of about 37%, and a glass transition temperature of about 60-65 degrees celcius provided excellent results.

The composition provided herein mimics both physical and mechanical characteristics of natural human bone. The nanocomposite composition has improved (i.e. reduced or non-existant) immunogenic responses and inflammatory reactions in vivo as compared to certain known bone graft materials. In certain embodiments, as detailed further below, the overall properties of the newly developed nanocomposite closely resemble the chemical properties of the trabecular bone, which makes the nanocomposite a suitable candidate for a wide range of bone repair applications.

While this invention is susceptible of embodiments in many different forms, there is shown in the drawings and will herein be described in detail several specific embodiments with the understanding that the present disclosure is to be considered as an exemplification of the principles of the invention and is not intended to limit the invention to the embodiments illustrated.

Following are specific examples of alterations in the composition materials, weight fractions and ratio of the constituents; preparation methods of the composition; chemical, thermal and mechanical properties of the nanocomposite; factorial designed statistical analysis of three of the most influential factors on the nanocomposite properties; and in vitro toxicity testing.

Example 1

Preparation of the First Class (MA Series) of Nanocomposite Composition

Poly (L-Lactide acid), PLLA, was purchased from Sigma-Aldrich ($M_w \geq 85$ KDalton, Lactel, USA) and directly used as matrix for production of composites. The PLLA, when purchased, had average molecular weight (Mw) of 85000 g/mol, 37% of crystallinity, a glass transition temperature ($T_g$) ranging 60 to 65° C. and degradation time greater than 24 months. Cotton source microcrystalline cellulose (MCC), with a mean particle size of 20 μm and an aspect ratio of 2-4, from Sigma-Aldrich (USA) was used as a reinforcing agent. Hydroxyapatite nanoparticles (HA) were obtained from Sigma-Aldrich (USA), having a mean particle size <200 nm, surface area of 14.3 (m$^2$/g) and a chemical formulation of $Ca_5(OH)(PO_4)$. Sodium Dodyl Sulphate (SDS), used as a coupling agent, was purchased from (Fluka, Canada). 1,4-Dioxane (Sigma-Aldrich, ACS Reagent, with purity ≥99%) ethanol (VWR, Canada, purity ≥99%) were used as solvents. Other solvents used in the process, notably, chloroform; hydrochloric acid; and nitric acid, were purchased from Sigma-Aldrich Chemical Co (Canada). All materials were used as received without further purification.

The MCC and HA were pretreated to aid in their homogeneous dispersal in the PLLA solution, to prevent them from agglomeration, and to encourage their covalent bonding with PLLA matrix b —COOH groups of SDS and $PO_4^{3-}$ or $Ca^{2+}$ groups of HA and —OH groups of MCC. The pretreatment of MCC and HA was done using a combination of two physical and mechanical methods. The PLLA was dissolved in 1,4-dioxane solution with the concentration of 5 mg/ml with the aid of vortex shaker and water bath at 60° C. HA nanoparticles was dispersed in water when purchased, in order to eliminate any trace of water, they freeze-dried for 72 hrs. Simultaneously, MCC and HA nanoparticles were then ultrasonicated in an ice-bath for 30 min at 4 mv with the presence of coupling agent (SDS) to decrease the size of the MCC crystals and obtain a homogeneous colloidal dispersion. The PLLA solution was then mixed with the mixture of pretreated MCC and HA homogeneous colloidal dispersion.

The procedure resulted in a stable, homogenous suspension of the nanoparticles. The resultant suspension was then molded, then frozen at −20° C., and finally the solvent was sublimated in a freeze-dryer at −54° C. under vacuum, yielding a porous composite nanostructure. The composite samples were placed in flask containing PBS (phosphate buffer saline) and shacked gently at 100 rpm for 12 h to remove the excess of SDS from the composite. This step was repeated two to five, preferably four times. Then sample was washed with distilled water using the same precedent procedure. Finally the samples were dried in a vacuum oven for 6 hours at 50° C.

Nanocomposite specimens were prepared according to various weight percentages indicated in Table 1.

TABLE 1

Composition in weight percent PLLA, MCC, HA and SDS of MA series of nanocomposites

| Sample Designation | PLLA (%) | MCC (%) | HA (%) | SDS (%) |
|---|---|---|---|---|
| Pristine | 100 | — | — | — |
| MA1010 | 76.9 | 7.7 | 7.7 | 7.7 |
| MA3030 | 52.6 | 15.8 | 15.8 | 15.8 |
| MA4040 | 45.45 | 18.18 | 18.18 | 18.18 |
| MA5050 | 40 | 20 | 20 | 20 |
| MA6060 | 35.5 | 21.5 | 21.5 | 21.5 |

Example 2

Modified Method of Preparation of Nanocomposite Composition

The method of Example 1 was repeated, with the following variations. First, a sequential solvent extraction of water (which can be present in the purchased HA material) was performed prior to the polymer concentrations being dispersed in 1,4-dioxane. This additional step was found to decrease the sedimentation and agglomeration of HA nanoparticles. A further variation was adding a surfactant, such as SDS, to the mixture of MCC and HA nanoparticles in 1,4-dioxane after the centrifuging step in the sequential solvent extraction and not before. This additional step prevented any negative effects of ultrasonication on the intermolecular-bonding between constituents of the colloid. A further variation to the method was the incorporation of salt particles as a porogen material, such as sodium chloride salt or sugar, during the preparation of the nanocomposite. It was observed that when the porogen particles leached out, they left "holes" in their absence, resulting in a more porous nanocomposite. This step was added into the fabrication of half of the specimens in order to increase the porosity of the nanocomposites, to control the morphology of the pores, and to create an inter-connective pores. The content of porogen was 40% of the weight of MCC and HA nanoparticles which was constant and equal to 0.5 g. Finally, it was also optional to remove excess coupling agent by floating the nanocomposite in water.

The MH series of nanocomposite specimens were prepared according to the composition designation indicated in Table 2.

TABLE 2

Nomenclature of MH series of nanocomposite specimens without and with the presence of a porogen

| Nomenclature of specimens | PLAA | MCC | HA | SDS | Concentration of PLLA in solvent (g/cc)% | Weight Ratio of MCC/HA | Presence of porogen |
|---|---|---|---|---|---|---|---|
| MH20 4 N | 57 | 22.5 | 6.5 | 14 | 20 | 4 | N[1] |
| MH20 1 N | 57 | 14 | 14 | 14 | 20 | 1 | N |
| MH20 0 N | 57 | 0 | 28 | 14 | 20 | 0 | N |
| MH20 4 P | 57 | 22.5 | 6.5 | 14 | 20 | 4 | P[2] |
| MH20 1 P | 57 | 14 | 14 | 14 | 20 | 1 | P |
| MH20 0 P | 57 | 0 | 28 | 14 | 20 | 0 | P |
| MH15 4 N | 50 | 26.6 | 6.6 | 16.8 | 15 | 4 | N |
| MH15 1 N | 50 | 16.6 | 16.6 | 16.8 | 15 | 1 | N |
| MH15 0 N | 50 | 0 | 33.3 | 16.8 | 15 | 0 | N |
| MH15 4 P | 50 | 26.6 | 6.6 | 16.8 | 15 | 4 | P |
| MH15 1 P | 50 | 16.6 | 16.6 | 16.8 | 15 | 1 | P |
| MH15 0 P | 50 | 0 | 33.3 | 16.8 | 15 | 0 | P |
| MH10 4 N | 40 | 32 | 8 | 20 | 10 | 4 | N |
| MH10 1 N | 40 | 20 | 20 | 20 | 10 | 1 | N |
| MH10 0 N | 40 | 0 | 40 | 20 | 10 | 0 | N |
| MH10 4 P | 40 | 32 | 8 | 20 | 10 | 4 | P |
| MH10 1 P | 40 | 20 | 20 | 20 | 10 | 1 | P |
| MH10 0 P | 40 | 0 | 40 | 20 | 10 | 0 | P |

[1](N) represents that no porogen involved in fabrication process; and
[2](P) represent that porogen is involved in fabrication process of the nanocomposites The fabrication guidelines in Table 1 and Table 2 are to be considered alterable. In general consideration, the compositions may be created so it can be applied to precasting, 3-D printing, or to a moldable state, or to a fluid state suitable for applications by injection. By adjusting the fluid volumes, material ratios, preparation conditions, and additives, the compositions according to the present invention may be tailored to a variety of applications, such as precast, moldable, or injectable alone or as a delivery vehicle; accelerated or retarded set; accelerated or retarded bioresorption. In certain embodiments, a range of formulations is desirable for a complete bone substitute.

Example 3

Fourier Transform Infrared Spectroscopic Analysis of Compositions

The chemical analysis of the prepared samples was performed using an Fourier Transform Infrared (FTIR) spectrometer (Nicolet Nexus 670, Corp, Madison, USA) equipped with a NIC (Ni—In—Cd) detector. The FTIR spectrum was measured in spectral range of 400-4000 $cm^{-1}$. The background data collected for a KBr blank were subtracted from each spectrum. Samples were mixed with KBr powder at room temperature. The standard spectral resolution of the instrument was between 0.16 $cm^{-1}$ and 0.5 $cm^{-1}$ suitable for most applications.

FTIR was implemented to evaluate the chemical interactions between the PLLA, the MCC and coupling agent (SDS). The intensity of —OH⁻ absorption peak of MCC at 3433 $cm^{-1}$ decreased after the incorporation of the coupling agent and MCC in nanocomposite. This change suggested formation of hydrogen bonding between —OH groups of MCC and Na+ groups of SDS. The area under the peak was relevant to the concentration of the functional group. The decrease of the intensity of the peak was indicative of the consumption of the functional groups involved in bond formation with OH groups of MCC by the aid of the coupling agent. The wave number between (900-1200 $cm^{-1}$) was attributed to the phosphate functional groups, the peaks at (866, 1411, and 1457 $cm^{-1}$) were ascribed to carbonate groups and a broad peak at (3571 $cm^{-1}$) belonging to hydroxyl (—OH) groups in HA. $PO^{3-}_4$ peaks of HA at 563, 602, 958, 1033 and 1092 $cm^{-1}$ shift to the right to 561, 601, 954, 1031, 1084 $cm^{-1}$ in the MCC/HA/PLLA/SDS composites as can be seen in FIG. 1. Peak shifting in FTIR spectra indicated some molecular interactions between the HA and PLLA. The results showed that the coupling agent encouraged PLLA and HA and MCC to ionize during the composite formation procedure causing COO⁻ of PLLA to bind with $Ca^{2+}$ of HA by the aid of the SDS; new carboxyl-calcium-carboxyl (COO⁻—[$Ca^{2+}$]—COO⁻) linkages appear to have been formed. All these molecular interactions suggested an increased and thus improved crystallinity of the composite and resultant improved mechanical properties.

Example 4

SEM Micrography of Compositions

The microstructure of the nanocomposite was examined using a Hitachi 2500 scanning electron microscope. All specimens were coated with a conductive layer of sputtered gold. The micrographs were taken at an accelerating voltage of 15 kV in secondary electron mode to ensure a suitable image resolution.

Figure 2:
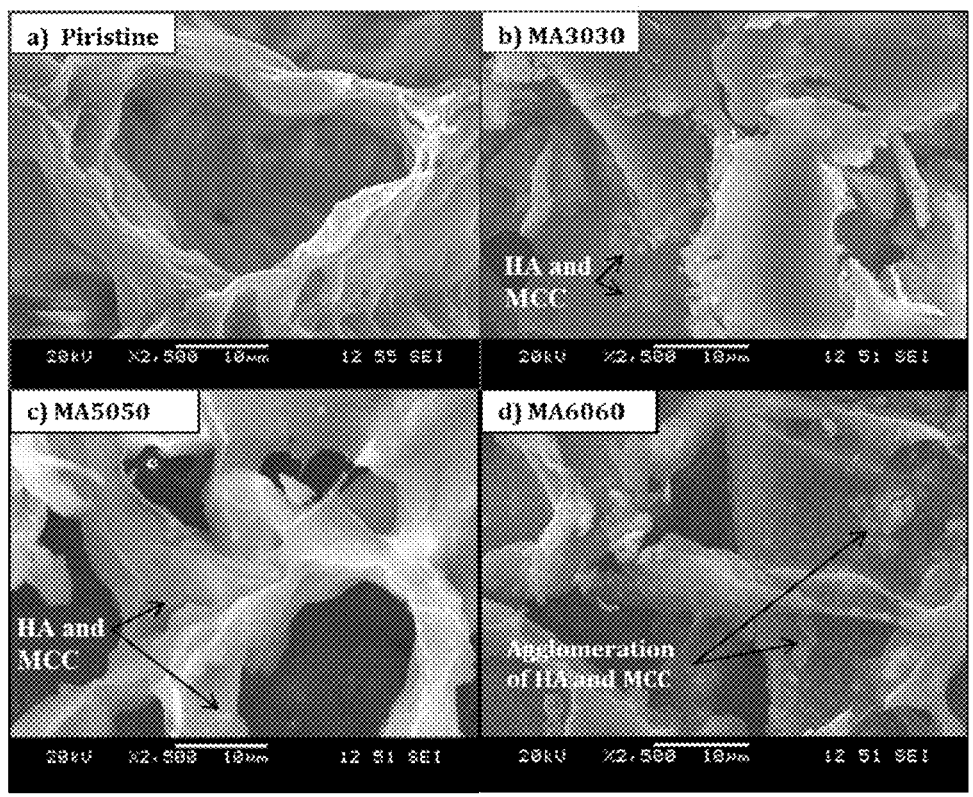
FIG. 2 shows SEM micrographs of certain nanocomposite compositions of the present invention.

The morphology and microstructure of the composites were exemplified in FIG. 2. The "pristine" sample (FIG. 2a) represents an internal porous structure formed by thermally induced phase separation. The SEM micrographs presented in FIG. 2b and FIG. 2c for MA3030, MA5050 respectively, revealed that HA nanoparticles and MCC fibers were successfully distributed in the matrix randomly and homogenously. Some were seen to be embedded in pore walls and some piled between pores, with no signs of agglomeration. FIG. 2d shows particle agglomerations in the MA6060 composite. Thus, the agglomeration of the nanoparticles appears to start occurring when the ratio of reinforcing agents to the polymer exceeds a value close to the ratio in the MA6060 composite. This agglomeration would likely undesirably affect the mechanical properties of the composites and make the composite more brittle and perhaps less optimal as artificial bone. The agglomeration may be attributed to the consumption of the functional groups of the PLLA or PLGA and the lower ability to form bonds with HA and MCC via the coupling agent (SDS).

Example 5

Differential Scanning Calorimetry

The crystallization and melting behavior of the prepared composites and neat PLLA were investigated using DSC (Diomand, PerkinElmers, USA) in Nitrogen atmosphere. A sample mass of approximately 6 mg was used for each sample. A heat-cool-heat regime was applied in this measurement and the second heating curve was used for thermal analysis. The sample was heated from 0° C. to 200° C. at a heating rate of 5° $C.\cdot min^{-1}$ before cooling it down to 0° C. using at a cooling rate of 50° $C.\cdot min^{-1}$. The sample was then re-heated to 200° C. again at a heating rate of 10° $C.\cdot min^{-1}$. The crystallinity of the prepared composites was obtained from equation (1):

$$\chi_c(\%) = \frac{\Delta H_m - \Delta H_c}{\Delta H_m^0 \times w} \times 100\% \quad \text{Equation (1)}$$

Where $\chi_c$ is the crystallinity, w is the weight fraction of PLLA in the composites, $\Delta H_m$ is the melting enthalpy calculated from DSC graph, $\Delta H_c$ is the recrystallization enthalpy and $\Delta H°_m$ is the melting enthalpy of pure crystalline PLLA (93.7 Jg$^{-1}$) [39].

To analyze the effect of the reinforcing agents on crystallinity of the PLLA, exothermic peak which is responsible for amorphous PLLA regions has been considered between (90-110° C.) at (1400-1600 sec) in order to calculate $\Delta$Hc and two endothermic peaks responsible for the melting of crystalline PLLA between (160-185° C.) at (2200-2600 sec) to calculate $\Delta$Hm$^1$ and between (50-70° C.) at (1100-1300 sec) to calculate $\Delta$Hm$^2$. While $\Delta$Hm=$\Delta$Hm$^1$+$\Delta$Hm$^2$. DSC analysis have been conducted on the MCC, SDS and HA separately in order to evaluate the influence of MCC and HA on the nanocomposite. The results showed that there is no peak from these raw materials that overlaps with the PLLA peaks.

In order to analyze the DSC graphs, normalization of each DSC thermograms is required in order to have the heat flow in Joule per gram of PLLA. The DSC software gives us the heat flow data Joule, in order to normalize it heat flow was divided by the weight of the nanocomposite sample used for DSC and multiplied by weight fraction of the PLLA in selected nanocomposite.

Figure 3:
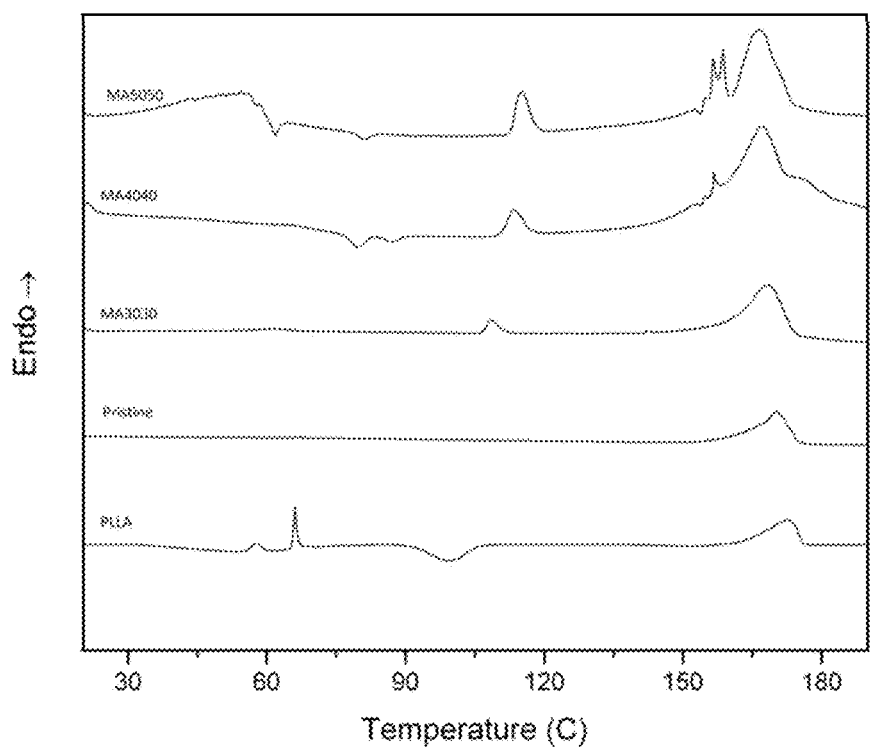
FIG. 3 shows DSC heating scans of PLLA and PLLA/MCC/HA nanocomposite compositions of the present invention.

A DSC study was performed on the pure PLLA and PLLA/HA/MCC composites with different weight ratio of MCC and HA to investigate the effect of MCC and HA nanoparticles on thermal behaviors of the PLLA matrix. The degree of crystallinity of the samples was evaluated by the crystallinity percentage of PLLA in the composites ($\chi_c$) and calculated using Equation 1. The DSC thermograms (shown in FIG. 3) suggested that there were changes in the thermal behavior of the composite with different compositions. The calculated $\chi_c$ from the thermograms was found in Table 3. The results showed the effect of increasing the weight ratio of MCC and HA nanoparticles on the crystallinity of the composites, which may cause a higher amount of ordered bonds via hydrogen bonding leading to an increase in the crystallinity. It is further observed that the single melting peak typical of the α-crystalline phase appearing between 150° C. and 180° C., changes to a double melting peak, indicating the melting of both the α'- and α crystalline phase in the DSC curves. The intensity of the exothermic peak clearly decreased with increasing the PLLA crystallinity. The re-crystallization phenomenon becomes negligibly small or disappears. The crystallinity of PLLA increased up to 90% by increasing the content of MCC and HA, while the corresponding exothermic peak responsible for the amorphous PLLA disappeared.

TABLE 3

Crystallinity of the PLLA and PLLA-MCC-HA composites derived from the heating DSC scans

| Sample | $W_{PLLA}$ (%) | $\Delta H^a_m$ (J/g) | $\Delta H^a_c$ (J/g) | $\Delta H^0_m$ (J/g) | $\chi$ (%) |
|---|---|---|---|---|---|
| Pristine | 100 | 47.51 | ~0 | 93.7 | 50 |
| MA3030 | 52.6 | 57.7 | −1.5 | 93.7 | 60 |
| MA4040 | 45.45 | 83 | −10.6 | 93.7 | 77 |
| MA5050 | 40 | 90.7 | −16 | 93.7 | 80 |

$^a$Values of Enthalpy are normalized to the weight of the PLLA in nanocomposites.

Example 6

Stress/Strain Testing of Compositions

The compressive strength and modulus of the porous nanocomposite with different compositions were measured using an electronic universal testing instrument (United, USA). The tests were performed using a 100N load cell and a crosshead speed of 1 mm/min. The tested specimens were cylindrical with a 13 mm diameter and 20 mm height. The specimens' surfaces were sandpapered using sandpapers with super fin grit size (P1200) in order to insure the contact with the top and bottom compression jigs. The compressive yield strength was defined as the cross point of the two tangent in stress-strain curve around the yield point. The compressive modulus was determined from the initial linear stress versus strain plot at strain <2%. Four samples were tested for each type of composite. All tests were conducted after washing the samples from the excess of SDS.

Figure 4:
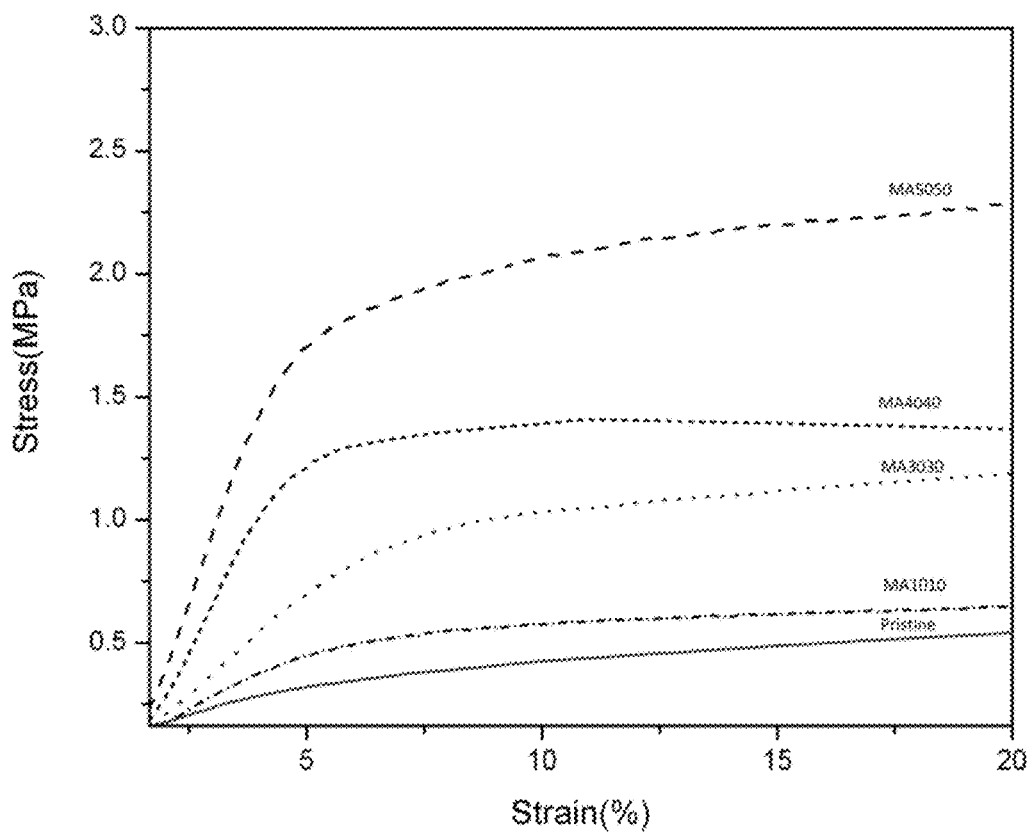
FIG. 4 shows a stress-strain curve of PLLA/MCC/HA compositions of the present invention, utilizing different weight ratios of MCC and HA.

Stress versus strain curves of PLLA/HA/MCC composites were presented in FIG. 4. The compressive strength and modulus of the composites showed a rising trend with higher concentration of PLLA. The determined values of the compressive strength and modulus of the composites were tabulated in Table 4. The experimental data revealed that the increase of the weight ratio of MCC from 0.1 to 0.5 lead to an improvement in the compressive yield stress from 0.127 (Pristine PLLA) to 2.2 MPa (MA5050) and the Young's modulus from 6.6 (Pristine PLLA) to 38 MPa (MA5050), respectively. Thus the increase of the weight fraction of MCC and HA from 0 to 20% of weight ratio of MCC increased the compression yield stress by 94% and the Young's modulus of the composites by 82%.

This significant increase may be attributed to the improvement of the interfacial bonding between the reinforcements and the polymer by increasing hydrogen bonding between the reinforcing agent (MCC or any plant-sourced cellulose nanofibres) and the PLLA or PLGA matrix. These results also confirm the FTIR observations. Increasing HA nanoparticles content may increase the crystallinity of the nanocomposite due to the presence of ordered hydrogen bonding and the ceramic nature of the HA leading to higher mechanical properties. For higher concentrations of reinforcing agents (greater than the concentration in MA5050) the composites became more brittle.

TABLE 4

Compression yield and Young's modulus of PLLA/MCC/HA composites

| Sample | Compression Yield Strength [MPa] (±Standard Deviation) | Young's Modulus [Mpa] (±Standard Deviation) |
|---|---|---|
| PRISTINE | 0.127 ± 0.027 | 6.5 ± 1 |
| MA1010 | 0.570 ± 0.071 | 10 ± 2 |
| MA3030 | 0.710 ± 0.060 | 17 ± 4 |
| MA4040 | 0.868 ± 0.113 | 23 ± 4 |
| MA5050 | 2.220 ± 0.106 | 38 ± 9 |

Example 7

Effect of Porogen

The effect of porogen content and the concentration of PLLA onto mechanical behaviour of the nanocomposites was studied. The nanocomposite specimens were prepared according to the compositions indicated in Table 2. Additionally, three independent factors were analyzed with three varying levels as shown in Table 5.

TABLE 5

Three independent variable (factors) and three levels

| Factors (variables) | Symbol | First level | Second level | Third level |
|---|---|---|---|---|
| Concentration of PLLA (g/cc) | A | 10 | 15 | 20 |
| Weight ratio of MCC/HA | B | 0 | 1 | 4 |
| Porogen content (% $W_t$)* | C | 0 | 40 | — |

*Porogen content equal to 0 replaced by N in nomenclature of specimens, and porogen content equal to 40 replaced by P.

The porosity measurement data revealed that the porosity of nanocomposites increased from 30 to 55-65% when the content of porogen increased from 0 to 40% $W_{PLLA}$.

Figure 5:
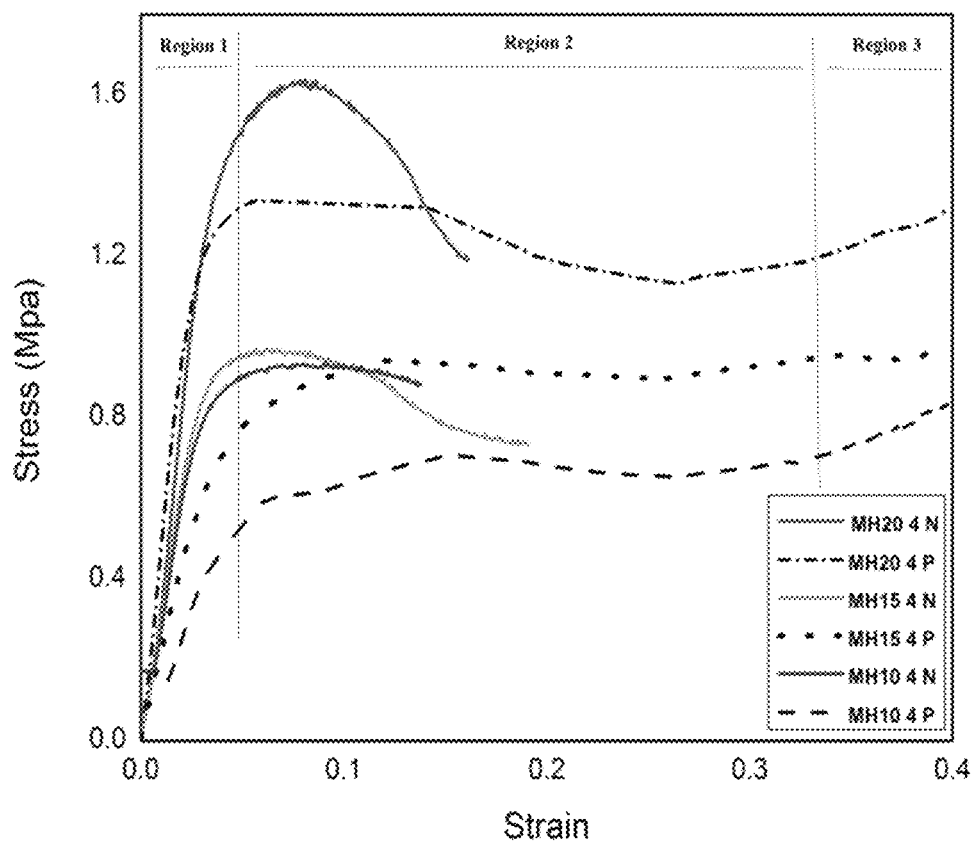
FIG. 5 shows stress-strain curves of the nanocomposites of the present invention, made with identical ratio of MCC/HA and various concentrations of PLLA and porogen.

FIG. 5 summarized the stress v. strain curve for compositions with three different PLLA concentrations, manufactured with (dashed) and without (solid) the use of a porogen. Adding porosity to the compositions significantly decreases compressive yield and Young's modulus, despite identical concentrations of PLLA and MCC/HA ratio. Thus the addition of porogen, like the modifications to PLLA and MCC/HA ratios in the compositions, can be a very useful tool for preparing artificial bone with various specific desired properties.

Example 8

Measuring Compressive Yield of Certain Compositions

Compressive yield for the MH20 4 N composition was found to drop from 0.12 MPa to 0.61 MPa, and 3.88 MPa to 20.07 MPa for Young's modulus. These values were calculated from stress-strain curves and illustrated in graphic form in FIGS. 6 and 7. These results show that the compressive yield dropped over 13% and Young's modulus dropped over 27% through the incorporation of the porogen within the nanocomposite fabrication process. This is related to the effect of increasing porosity leading to the weakening of the mechanical strength. The porogen content (porosity percentage) affected the Young's modulus more than compressive yield. This was also confirmed using statistical analysis.

The influence of the porogen on the shape of the stress-strain curve was evident by the formation of large strain intrinsic deformation behaviour of PLLA polymer observed as a result of uniaxial compression test in nanocomposites with more porous structure by comparing the colourful curves and the dashed-line curves in FIG. 5, which shows a large strain deformation region identified as region 2 and region 3 in dashed-line curves. Nanocomposites with higher porosity showed extended ductility zone in their stress-strain curve. Essentially, FIGS. 5-7 illustrate that the addition of the porogen results in a more porous composite, resulting in less brittle failure and suppression of crack propogation, allowing the material to behave more plastically.

Example 9

Effect of PLLA Concentration on Compositions

Figure 6:
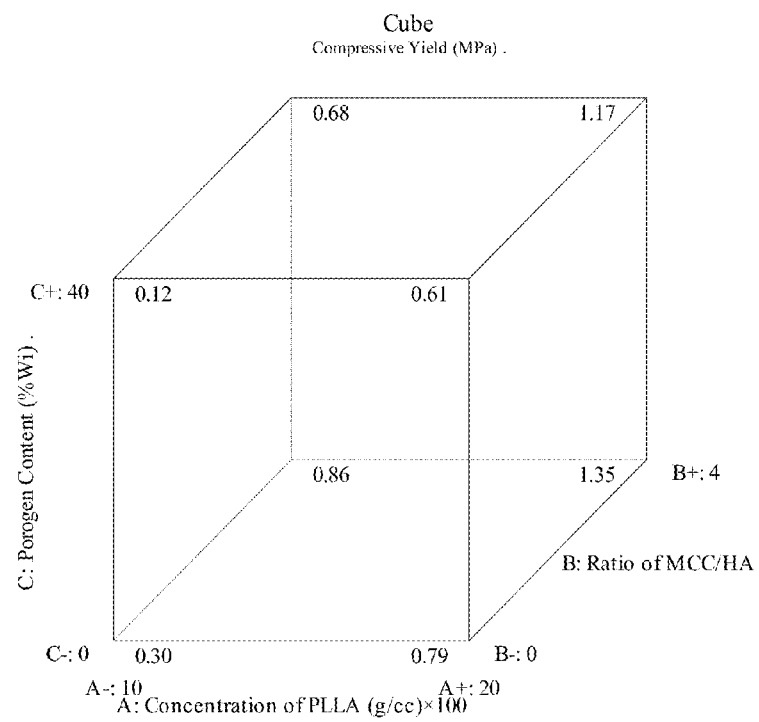
FIG. 6 shows results of compressive yield versus concentration of PLLA (factor A), ratio of MCC/HA (factor B), and content of porogen (factor C), for various compositions of the present invention.
Figure 7:
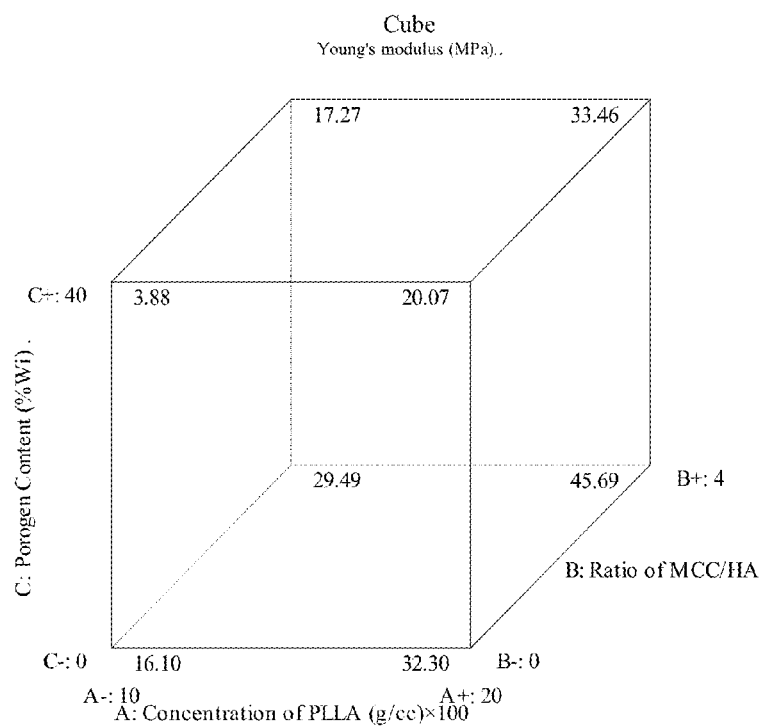
FIG. 7 shows results of Young's modulus versus concentration of PLLA (factor A), ratio of MCC/HA (factor B), and content of porogen (factor C), for various compositions of the present invention.

FIG. 6 demonstrates that by increasing the concentration of PLLA from 10% to 20%, the compressive yield of the nanocomposites fabricated with incorporation of no porogen, increased from 0.3 MPa to 0.79 MPa. Consequently, the Young's modulus improved from 16.1 MPa to 29.49 MPa for the same nanocomposites as can be seen from FIG. 7.

By increasing the concentration of PLLA in the nanocomposites, the respective values of compressive yield in FIG. 6 and the Young's modulus in FIG. 7 (having the same ratio of MCC/HA), increased. Increasing the number of PLLA chains affected the overall strength of the nanocomposite by providing more mechanical strength and more potential sites for chemical bonding with HA nanoparticles and cellulose crystals via the coupling agent.

Example 10

Effect of HA on Mechanical Behavior of Compositions

Nanocomposites with 0% $W_t$ of MCC (ratio of MCC/HA=0) and with or without addition of SDS were investigated separately in order to study the effect of HA nanoparticles on the mechanical behaviour of the nanocomposites. The PLLA-HA nanocomposites showed compressive yield about 0.39 MPa and Young's modulus of 10.9 MPa. The values extracted from FIG. 6 and FIG. 7 for compressive yield and Young's modulus PLLA-HA-SDS nanocomposites (Ratio of MCC/HA=0) showed improved mechanical properties in comparison with the non-SDS compositions, indicating that even the addition of SDS, in the absence of cellulose, significantly improved prior art compositions. The MH20 0 N nanocomposites, had a compressive yield of 0.79 MPa and Young's modulus is 32 MPa, and for MH20 0 P nanocomposites which have the same composition (Factor A=20, Factor B=0) as MH20 0 N nanocomposites but were more porous, the compressive yield dropped to 0.61 MPa and the Young's modulus to 20 MPa, which was greater than prior art PLLA-HA composites. This improvement was likely related to the incorporation of the coupling agent (SDS) and the presence of strong interfacial bonding between HA nanoparticles and PLLA polymer. The molecular interactions not only improve the interfacial bonding of nanoparticles to the matrix, but also enhance their dispersion homogeneity as well, which in turn enhanced the mechanical properties of the nanocomposite.

Example 11

Stress Strain Curves for HA Concentration

Figure 8:
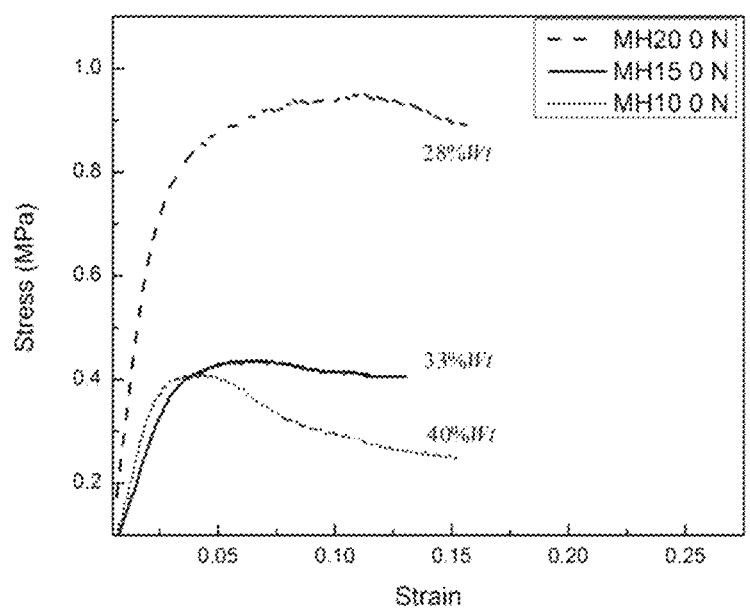
FIG. 8 shows stress-strain curve for nanocomposites reinforced by HA nanoparticles solely (ratio MCC/HA=0).

Stress-strain curves represented in FIG. 8 demonstrated the influence of increasing the weight fraction of HA by increasing the concentration of PLLA onto the shape of their corresponding stress-strain curve. It can be seen from FIG. 8 that the nanocomposite with the lowest content of HA (28 $W_t$ %) had the highest mechanical strength. Also, it is clear from FIG. 8, by decreasing the content of HA nanoparticles from 40 to 28 $W_t$ % (from down to up), the area under the stress-strain curve increased. The area under the stress-strain curve represents the absorbed energy of the specimen before breaking. The highest amount of HA tested resulted in a brittle fracture and lower absorbed energy before break.

While performing compression testing, it was observed that the fracture occurred in a brittle manner through the initiation and propagation of the oblique sharp cracks from the exterior corners of the specimen wall. The surface modification of the bioceramic nanoparticles such as clays and hydroxy apatite nanoparticles both increased the basal spacing of clays, thereby increasing the ease of entry of polymers, and served as a compatibilizer between the hydrophilic clays and the hydrophobic polymer. By modifying the surface of the cellulose microcrystals and hydroxyapatite nanoparticles through the use of coupling agent (SDS), high aspect ratio of reinforcing agents (MCC and HA) were incorporated into a polymer matrix. However, an overall enhancement of Young's modulus was observed due to the addition of rigid bioceramic reinforcing agent with high Young's modulus.

Example 12

Compressive Yield and MCC/HA Ratio

Figure 9:
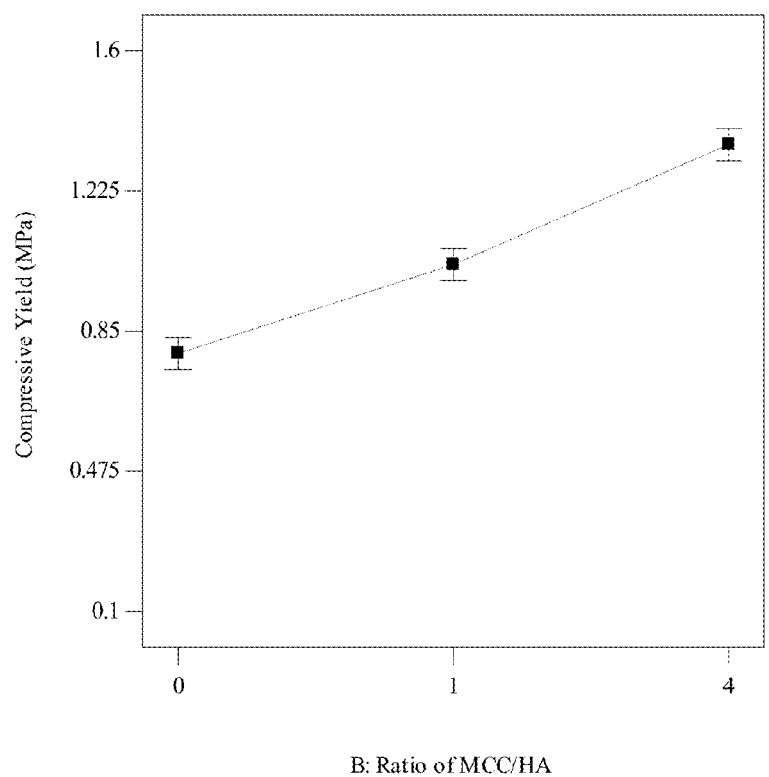
FIG. 9 shows compressive yield versus ratio of the MCC/HA of nanocomposites with concentration of PLLA (A=20), zero porogen content (C=0), for various compositions of the present invention.

FIG. 9 shows that when the cellulose microcrystals (MCC) were incorporated into the composition of the nanocomposites, the compressive yield increased. Specifically, by increasing the ratio of MCC/HA from 0 to 4, the compressive yield of the nanocomposites increased from 0.79 to 1.35 MPa for nanocomposites with no porogen involved in their fabrication procedure. This improvement is related to the reinforcing effect of MCC, which amplified the reinforcing effect of HA nanoparticles. Furthermore, the improvement of strength of the nanocomposites strongly depends on the polymer, the reinforcing agents compatibility, and the molecular interactions between them. The strong interfacial interaction and compatibility increase stress transfer to the reinforcing agents resulting in the higher load-bearing ability of the MCC containing nanocomposites.

Example 13

Measurement of Absorbed Water

Figure 10:
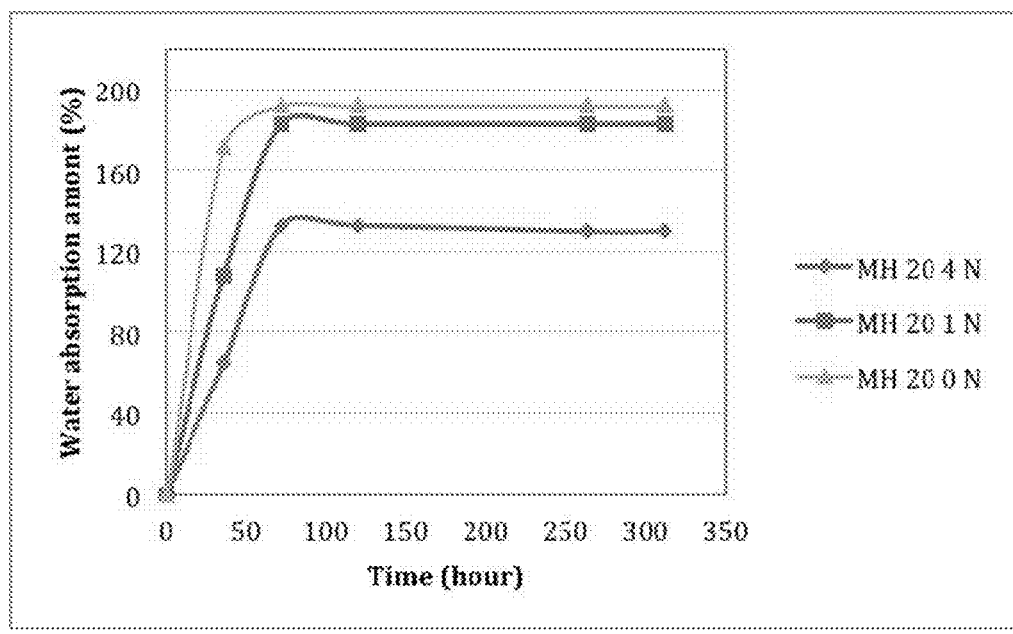
FIG. 10 shows water absorption curves nanocomposites with different content of cellulose (B=ratio of MCC/HA=0, 1, 4) and the same content of PLLA (A=Concentration of PLLA=20), for various compositions of the present invention.

The amount of absorbed water in the nanocomposites was analyzed by calculating the weight difference between the samples exposed to water and the dried samples. The amount of absorbed water plotted against time for all the samples was illustrated in FIG. 10. For all of the samples, water absorption reached a certain value, saturated, and leveled off during the first time window (0-72 h). The hydrophilic character of hydroxyapatite nanoparticles and natural fibers was believed to be responsible for the water absorption in the nanocomposites. As can be seen from FIG. 10, MH 20 4 N (the blue curve) had the longest water saturation time and lowest amount of absorbed water. Since MH 20 4 N nanocomposites had the highest ratio of MCC/HA, it can be surprisingly concluded that when the fiber content was increased, the saturation time was prolonged.

Example 14

Cellulose Content Affects Absorbed Water

Figure 11:
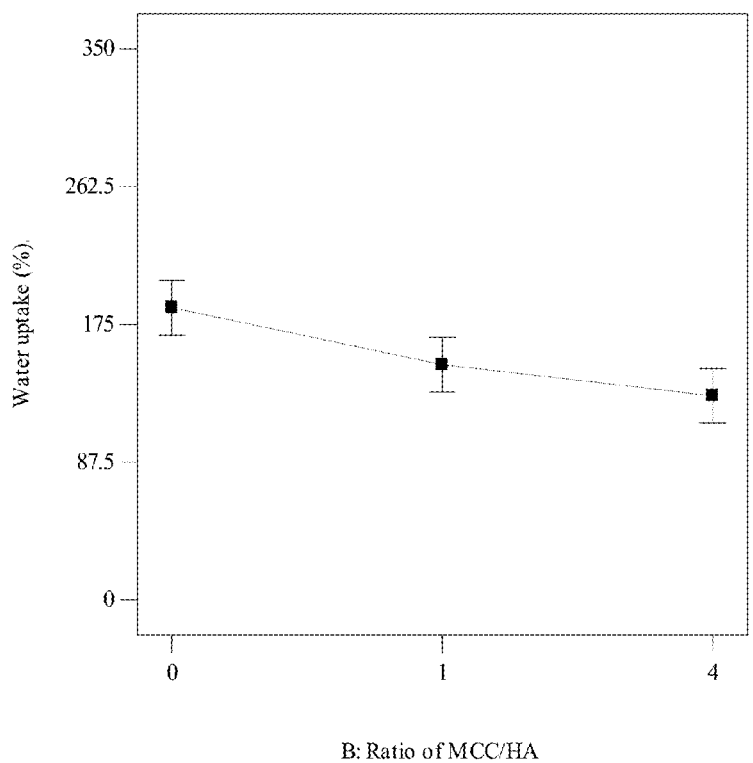
FIG. 11 shows the effect of ratio of MCC/HA (B) onto water absorption of the (MH 20 0 N), (MH 20 1 N), and (MH 20 4 N) nanocomposites which have various ratio of MCC/HA, but identical concentration of PLLA equal to 20 (A=20) and porogen content equal to zero.

As can be seen from FIG. 11, MH 20 0 N nanocomposites with zero content of cellulose (B=Ratio of MCC/HA=0) demonstrated the highest absorbed water amount, between 178-188% and nanocomposites with highest ratio of cellulose over hydroxyapatite (factor B=ratio of MCC/HA=4) showed the least amount of absorbed water around 80%, when saturated. This suggests improved compatibility of cellulose microcrystals and the PLLA matrix interface due to the presence of the coupling agent (SDS) and the optimum ratio of MCC over HA. SDS possesses one hydrophilic tail of carboxylic groups that can bind to the cellulose microcrystals and hydroxy apatite nanoparticles on one side, and a hydrophobic head that can interact with the polymeric matrix (PLLA). The water absorption resistance increased by increasing the content of natural fiber was a desirable result. As described, one of the important challenges in the case of natural fiber nanocomposites is improving their water resistance by increasing the content of natural fibers. Since the absorbed water amount has a direct relationship with the biodegradation rate, the nanocomposites with the highest content of cellulose will show the slowest biodegradation rate.

Based on this model, with better adhesion between the matrix and fibers, the velocity of the diffusional processes decreased since there are fewer gaps in the interfacial region and also more hydrophilic groups are involved in the reaction with the coupling agent blocks hydroxyls. Surprisingly, the results show that the presence of higher porosity to the existence of voids can accelerate the diffusion, and a higher content of fibers leads to a higher amount of water absorbed.

Figure 12:
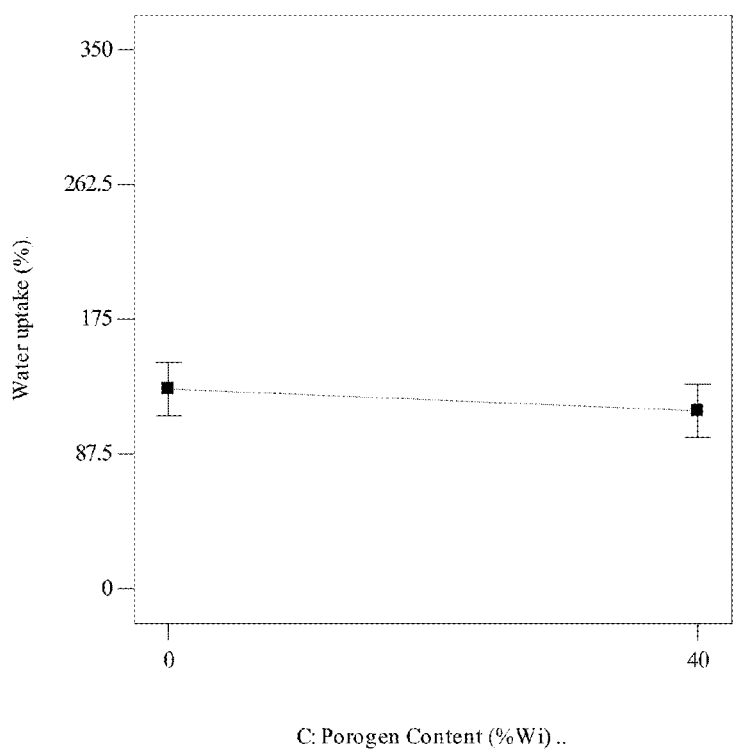
FIG. 12 shows the effect of porogen content onto water absorption ability of the (MH 20 4 N), (MH 20 4 P) nanocomposites which have identical ratio of MCC/HA equal to 4 (B=4) and identical concentration of PLLA equal to 20 (A=20) but different porogen content.

Furthermore, results shown in FIG. 12 indicate that water absorption does not appear to relate to the porosity of the composition. By increasing the porosity through the utilization of porogen, the amount of absorbed water remained almost the same. These experimental results indicate the water absorption behaviour of the nanocomposite is directly affected by the type of the constituents and fibers, their content and the strength of bonding with the polymeric matrix and other constituents, which will finally result in better compatibilization between fibers and matrix. MH 20 4 N series of nanocomposites with higher content of cellulose over hydroxyapatite (Ratio of MCC/HA=4), showed the lowest water absorption percentage as compared with the others, which showed higher values of compressive yield and Young's modulus.

Example 15

Statistical Analysis of Compressive Yield

A design of experiments and ANOVA statistical analysis of the compressive yield ($\sigma_y$) was carried out utilizing a trial version of Design-Expert software 7.0.0 (Stat-Ease Inc.). The nanocomposite specimens were prepared according to the compositions indicated in Table 2. Three replicate of each composition were fabricated separately and coded based on their experiment run order. Total 56 fabricated specimens characterized to evaluate their final properties.

Table 6 shows the ANOVA statistical terms for compressive yield of nanocomposites. The F-value in ANOVA table is a reliable criterion for ranking of the factors with respect to their influence on particular response. A higher value of a calculated F-value for a factor means a greater influence of that factor on the evaluated response. It is clear from Table 6 that the most important contributing factor on the variability of the results is the ratio of MCC/HA (B) with an F-value of 175.66 and then the concentration of PLLA (A) with a F-value of 135.68. The porogen content (C) with an F-value of 53.15 has the least effect on the compressive yield equation. Besides, the model F-value of 135.17 implies that the model is significant. The final equation for compressive yield in terms of coded factors is presented as Equation 4:

$$\text{Compressive Yield} = +0.71 - 0.23 \times A[1] - 0.028 \times A[2] - 0.27 \times B[1] - 0.028 \times B[2] - 0.089 \times C \quad \text{Equation (4)}$$

Moreover, Table 7 represents the standard deviation information of evaluated responses. The "Predicted R-Squared" of 0.7981 is in reasonable agreement with the "Adjusted R-Squared" of 0.8970. "Adequate precision" measures the signal to noise ratio. A ratio greater than 4 is desirable. Adequate precision ratio of 41.018 indicates an adequate signal. This model can be used to navigate the design space.

TABLE 6

ANOVA table for compressive yield ($\sigma_y$)

| Factors | df[a] | Sum of squares | Mean square | F-value | p-value |
|---|---|---|---|---|---|
| Model | 5 | 5.45 | 1.09 | 135.17 | <0.0001 |
| Concentration of PLLA (A) | 2 | 2.19 | 1.09 | 135.68 | <0.0001 |
| Ratio of MCC/HA (B) | 2 | 2.83 | 1.42 | 175.66 | <0.0001 |
| Porogen content (C) | 1 | 0.43 | 0.43 | 53.15 | <0.0001 |
| Residual | 0.58 | 72 | 8.06E−003 | — | — |
| Lack of fit | 0.29 | 36 | 8.06E−003 | 1.00 | 0.5000 |
| Pure error | 0.29 | 36 | 8.06E−003 | — | — |

[a] Degree of freedom

TABLE 7

Error of compressive yield ($\sigma_y$)

| | Response | | | | |
|---|---|---|---|---|---|
| | Standard dev. | Mean | R-Squared | Adjusted R-squared | Predicted R-Squared | Adequate R-Squared |
| Compressive yield | 0.090 | 0.71 | 0.9037 | 0.8970 | 0.7981 | 41.018 |

Example 16

Statistical Analysis of Young's Modulus

A design of experiments and ANOVA statistical analysis of Young's modulus (E) was carried out utilizing a trial version of Design-Expert software 7.0.0 (Stat-Ease Inc.). The nanocomposite specimens were prepared according to the compositions indicated in Table 2. Three replicate of each composition were fabricated separately and coded based on their experiment run order. Total 56 fabricated specimens characterized to evaluate their final properties.

Table 8 shows the ANOVA statistical terms for Young's modulus of the nanocomposites. It is clear from Table 8 that the most important contributing factor for the variability of the results is the porogen content with a F-value of 275.01 and the ratio of concentration of PLLA with a F-value of 184.04. The ratio of MCC/HA with an F-value of 122.57 has the least effect on Young's modulus equation. The Model F-value of 177.65 implies the model is significant. The Final equation of Young's modulus in terms of coded factors represented in Equation 5:

$$\text{Young's modulus} = +21.70 - 6.33 \times A[1] - 3.54 \times A[2] - 5.38 \times B[1] - 2.62 \times B[2] - 6.11 \times C \quad \text{Equation (5)}$$

Table 9 represents the standard deviation information of Young's modulus. The "Predicted R-Squared" of 0.8504 is in reasonable agreement with the "Adjusted R-squared" of 0.9198. "Adequate precision" measures the signal to noise ratio. A ratio greater than 4 is desirable. The ratio of 46.310 indicates an adequate signal. So, this model can be used to navigate the design space.

TABLE 8

ANOVA table for Young's modulus (E)

| Factor | df[a] | Sum of squares | Mean square | F-value | p-value |
|---|---|---|---|---|---|
| Model | 5 | 6515.44 | 1303.09 | 177.65 | <0.0001 |
| Concentration of PLLA (A) | 2 | 2700.05 | 1350.02 | 184.04 | <0.0001 |
| Ratio of MCC/HA (B) | 2 | 1798.11 | 899.06 | 122.57 | <0.0001 |
| Porogen content (C) | 1 | 2017.28 | 2017.28 | 275.01 | <0.0001 |
| Residual | 72 | 528.14 | 7.34 | — | — |
| Lack of fit | 36 | 264.07 | 7.34 | 1.00 | 0.5000 |
| Pure error | 36 | 264.07 | 7.34 | — | — |

[a] Degree of freedom

TABLE 9

Error of Young's modulus (E)

| | Response | | | | |
|---|---|---|---|---|---|
| | Standard dev. | Mean | R-Squared | Adjusted R-squared | Predicted R-Squared | Adequate R-Squared |
| Young's modulus | 2.71 | 21.70 | 0.9250 | 0.9198 | 0.8504 | 46.310 |

Example 17

Statistical Analysis of Water Uptake Ability

A design of experiments and ANOVA statistical analysis of the water uptake ability was carried out utilizing a trial version of Design-Expert software 7.0.0 (Stat-Ease Inc.). The nanocomposite specimens were prepared according to the compositions indicated in Table 2. Three replicate of each composition were fabricated separately and coded based on their experiment run order. Total 56 fabricated specimens characterized to evaluate their final properties.

Table 10 shows the ANOVA statistical terms for the water uptake ability of the nanocomposites. The F-value obtained from ANOVA statistical analysis shows that the most important contributing factor on the variability of the results is the concentration of PLLA (A) with an F-value of 16.35 and then the ratio of MCC/HA (B) with an F-value of 11.04. The porogen content (C) with an F-value of 2.06 has the least effect on the water uptake ability equation. The final equation for water uptake ability in terms of coded factors is presented as Equation 6:

$$\text{Water uptake} = +185.91 + 29.48 \times A[1] + 8.59 \times A[2] + 30.76 \times B[1] - 5.46 \times B[2] - 7.09 \times C \quad \text{Equation (6)}$$

Moreover, Table 11 represents the standard deviation information of evaluated responses. The "Predicted R-Squared" of −0.0556 is in reasonable agreement with the "Adjusted R-Squared" of 0.4023. "Adequate precision" measures the signal to noise ratio. A ratio greater than 4 is desirable. An Adequate precision ratio of 11.389 indicates an adequate signal. This model can be used to navigate the design space.

Specimens with the lowest content of HA nanoparticles and the highest content of MCC (a ratio of MCC/HA of 4) showed the highest mechanical strength. The apparent ductility was observed in the stress-strain curve of the compositions with higher porosity. By increasing the ratio of MCC/HA from 0 to 4, the amount of absorbed water significantly decreased. It appears that the level of compatibility between reinforcing agents and the matrix has significant effect on the water absorption behavior.

TABLE 10

ANOVA table for water uptake ability of nanocomposites

| Factors | df[a] | Sum of squares | Mean square | F-value | p-value |
|---|---|---|---|---|---|
| Model | 5 | 74869.54 | 14973.91 | 11.37 | <0.0001 |
| Concentration of PLLA (A) | 2 | 43067.54 | 21533.63 | 16.35 | <0.0001 |
| Ratio of MCC/HA (B) | 2 | 43067.26 | 14542.91 | 11.04 | <0.0001 |
| Porogen content (C) | 1 | 2716.46 | 2716.46 | 2.06 | 0.1553 |
| Residual | 72 | 94854.67 | 1317.43 | — | — |
| Lack of fit | 36 | 47427.33 | 1317.43 | 1.00 | 0.5000 |
| Pure error | 36 | 47427.33 | 1317.43 | — | — |

[a] Degree of freedom

TABLE 11

Error of water uptake ability

| | | Response | | | |
|---|---|---|---|---|---|
| Standard dev. | Mean | R-Squared | Adjusted R-squared | Predicted R-Squared | Adequate R-Squared |
| Water uptake 36.30 | 185.91 | 0.4411 | 0.4023 | −0.0556 | 11.389 |

Example 18

Biocompatibility and Cytotoxicity of Compositions

The toxicity of the compositions prepared in Example 1 was evaluated in a Methyl tetrazolium (MTT) reduction assay. Composite extracts were evaluated against URM-106 osteoblast using the MTT assay in 96-well plates. Selected samples were cut to cylindrical shapes with diameter of 13 mm and length of 2 mm. Sterilization was done by autoclaving (Heidoplph, USA). Samples were prepared for culture by autoclave sterilization at 121° C. for 45 minutes at 2 atm. Rat cells line URM-106 (Osteosarcoma, ATCC) were used in this study. Cells were grown at 37° C. in a 5% $CO_2$ humidified atmosphere in Dulbecco Minimal Essential Medium (DMEM), supplemented with 10% fetal bovine serum (FBS), 1% penicillin streptomycin (PS) and 2 mML-glutamine at 5% $CO_2$ and 37° C. Each sample was immersed in DMEM as an extracting media with an extraction medium volume to surface area ratio of 1.25 ml/cm² at 5% $CO_2$ and 37° C. Extraction was completed over 24 hours, at which point the extraction media was removed and centrifuged before being applied to cell cultures. URM-106 was detached from the culture using Trypsin/EDTA (Ethylenediaminetetraacetic acid) and subsequently pelleted by centrifugation. Cells were re-suspended to a concentration of $1 \times 10^4$ cells/ml, and 100 μl of this suspension was added per well to a 96 well plate. Cells were allowed to adhere for 24 hrs, 46 hrs, and 72 hrs at 37° C. in a 5% CO2 atmosphere, before media aspirated. Extraction media were added to the well plate and maintained at 37° C. in a 5% $CO_2$ atmosphere.

Control samples consisted of URM-106 cells grown on tissue cultures plastic (TCP) supplemented with complete DMEM not in contact with extracts. After 24 hrs of incubation periods, the extracts were removed and each well was treated with the MTT solution for 4 hrs at 5% $CO_2$, 37° C. The medium was removed and then 100 μL of Dimethyl Sulfoxide was subsequently added to each well, and the plate was shaken for 5 min before reading at 590 nm on a microplate reader. Toxicity was calculated as the percentage of control cell viability.

Figure 13:
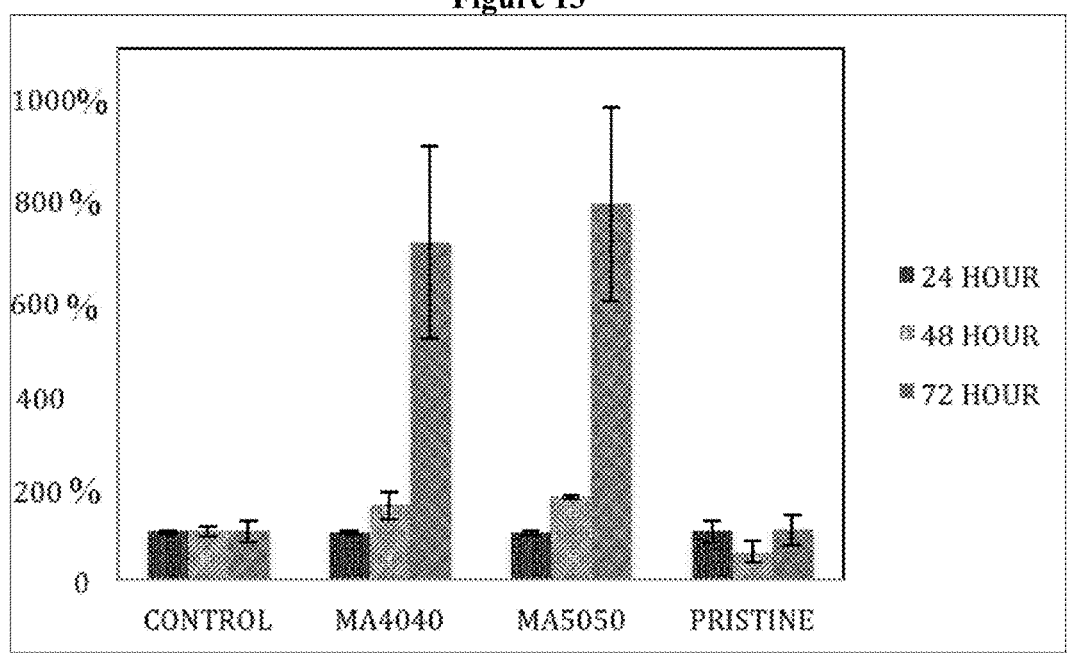
FIG. 13 shows cells viability of URM-106 cells after incubation in extracts of MA4040, MA5050, and pristine specimens for 24, 48, and 72 h. Tissue culture plastic (TCP) with no biomaterial extract was the control group. Results are expressed as % of control for all.

The results of calculation of cells viability are represented in FIG. 13 for cytotoxicity after 24 h exposure of cells to three sample test groups and control sample (with no extract). Cells viability generally was not affected significantly after 24 h, 48 hrs, and 72 hrs incubation time for all studied extracts compared to the control. For MA5050, proliferation rate seems to be the highest. As can be seen from FIG. 13, after 24 hrs, 48 hrs, and 72 hrs culturing the cells in the extract of nanocomposite, not only remained alive but also proliferated.

The present teachings enable the manufacture of artificial bone or nanocomposite useful for bone grafting or replacement. The strength, porosity, water absorption, and elasticity of the composition can be tailor designed, within the parameters taught herein, to achieve a close match to the bone being replaced or grafted to. The exemplified embodiments hereindescribed would all be suitable for use as artificial bone. Other embodiments within the general teachings are contemplated.

Throughout this application, various publications, including United States patents, are referenced by patent number. Full citations for the publications are listed below. The disclosures of these publications and patents in their entireties are hereby incorporated by reference into this application in order to more fully describe the art to which this invention pertains.

The invention has been described in an illustrative manner, and it is to be understood that the terminology that has been used is intended to be in the nature of the words of description rather than of limitations.

Many modifications and variations of the present invention are possible in light of the above teachings. The foregoing parts, embodiments and figures are presented by way of example only; the scope of the present invention is not to be strictly limited to the parts and example embodiments provided. It is, therefore, to be understood that within the scope of the appended claims, the invention may be practiced otherwise than as specifically described.

The invention claimed is:

1. A composition comprising:
   (a) Poly L-Lactide acid (PLLA), or poly glycolic acid (PLGA);
   (b) cotton sourced micro or nano scale cellulose crystals or fibers;
   (c) hydroxyapatite (HA) nanoparticles having a mean particle size of less than 200 nm; and
   (d) a coupling agent.

2. The composition of claim 1 wherein the composition is in the form of a porous nanocomposite matrix.

3. The composition of claim 1 wherein the cotton sourced micro or nano scale cellulose crystals or fibers are a cotton sourced microcrystalline cellulose (MCC).

4. The composition of claim 1 wherein the coupling agent is an anionic surfactant.

5. The composition of claim 4 wherein the coupling agent is sodium dodecyl sulphate (SDS).

6. The composition of claim 1 wherein the weight fraction of PLLA is 40 to 60 $W_t\%$.

7. The composition of claim 3 wherein the summation of the weight fraction of MCC+HA is 20 to 40 $W_t\%$.

8. The composition of claim 5 wherein the weight fraction of SDS is 10 to 20 $W_t\%$.

9. The composition of claim 3 wherein the weight ratio of MCC to HA is 1:1 to 4:1.

10. The composition of claim 1 wherein the micro or nano scale cellulose crystals or fibers have a mean particle size of less than 20 μm and an aspect ratio of less than 4.

11. The composition of claim 1 wherein the HA nanoparticles have a surface area of about 14 $m^2/g$.

12. The composition of claim 1 wherein the PLLA has an average molecular weight of at least about 85000 g/mol, a crystallinity of about 37%, and a glass transition temperature of about 60-65° C.

13. An artificial bone substitute, graft or filling comprising the composition of claim 1.

14. A trabecular bone substitute, graft or filling comprising the composition of claim 1.

15. A 3-D printed patient-tailored bone substitute or a 3-D printed biodegradable biomaterial, or a fractured bone fixation instrument such as a biodegradable screw, comprising the composition of claim 1.

16. A porous nanocomposite matrix composition consisting of:
(a) poly L-Lactide acid (PLLA), or poly glycolic acid (PLGA);
(b) cotton sourced micro or nano scale cellulose crystals or fibers;
(c) hydroxyapatite (HA) nanoparticles having a mean particle size of less than 200 nm; and
(d) a coupling agent.

17. A porous nanocomposite matrix composition consisting of:
(a) 40-57 $W_t$% poly L-Lactide acid (PLLA);
(b) cotton sourced microcrystalline cellulose (MCC) having a mean particle size of less than 20 μm and an aspect ratio of less than 4;
(c) hydroxyapatite (HA) nanoparticles having a mean particle size of less than 200 nm and a surface area of about 14 $m^2/g$;
(d) 14-20 $W_t$% sodium dodecyl sulphate;
wherein the summation of the weight fraction of MCC+HA is 29 to 40 $W_t$% and the weight ratio of MCC to HA is 1:1 to 4:1.

* * * * *